(12) United States Patent
Heckel et al.

(10) Patent No.: US 6,545,035 B1
(45) Date of Patent: Apr. 8, 2003

(54) SUBSTITUTED INDOLINONES WITH KINASE INHIBITORY ACTIVITY

(75) Inventors: Armin Heckel, Biberach (DE); Rainer Walter, Biberach (DE); Wolfgang Grell, Biberach (DE); Jacobus C. A. Van Meel, Moedling (AU); Norbert Redemann, Biberach (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/969,912

(22) Filed: Oct. 3, 2001

Related U.S. Application Data

(62) Division of application No. 09/323,499, filed on Jun. 1, 1999, now Pat. No. 6,319,918.
(60) Provisional application No. 60/092,014, filed on Jul. 8, 1998.

(30) Foreign Application Priority Data

Jun. 4, 1998 (DE) .......................... 198 24 922

(51) Int. Cl.⁷ .................. A61K 31/4035; A61K 31/404; A61P 35/00; C07D 403/12
(52) U.S. Cl. .................. 514/414; 548/455; 548/467
(58) Field of Search .................. 548/467, 455; 514/414

(56) References Cited

U.S. PATENT DOCUMENTS 4,145,422 A    3/1979   Winn et al.

FOREIGN PATENT DOCUMENTS

| BE | 838 623 A | 6/1976 |
|----|-----------|--------|
| WO | WO 96 40116 A | 12/1996 |
| WO | WO 98 07695 A | 2/1998 |
| WO | WO 99 15500 A | 4/1999 |

*Primary Examiner*—Robert W. Ramsuer
(74) *Attorney, Agent, or Firm*—Robert P. Raymond; Alan R. Stempel; Mary-Ellen M. Devlin

(57) ABSTRACT

Substituted indolinones of general formula

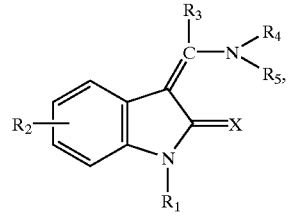

(I)

having effect on various kinases and cycline/CDK complexes and on the proliferation of various tumour cells. Exemplary compounds are:

3-Z-[1-(4-(N-Benzyl-N-methyl-aminomethyl)-phenylamino)-1-methyl-methylene]-5-amido-2-indolinone and 3-Z-[1-(4-(2,3,4,5-Tetrahydro-benzo(d)azepin-3-yl-methyl)-phenylamino)-1-methyl-methylene]-5-amido-2-indolinone.

10 Claims, No Drawings

SUBSTITUTED INDOLINONES WITH KINASE INHIBITORY ACTIVITY

RELATED APPLICATIONS

This is a division of Ser. No. 09/323,499, filed Jun. 1, 1999 now U.S. Pat. No. 6,319,918, claiming benefit of prior provisional application Ser. No. 60/092,014, filed on Jul. 8, 1998.

DESCRIPTION OF THE INVENTION

The present invention relates to new substituted indolinones of general formula

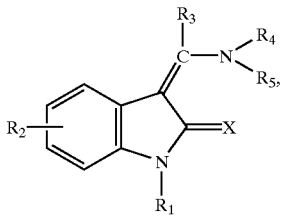

(I)

the isomers thereof and the salts thereof, particularly the physiologically acceptable salts thereof which have valuable properties.

The above compounds of general formula I wherein $R_1$ denotes a hydrogen atom or a prodrug group have valuable pharmacological properties, particularly an inhibitory effect on various kinases, particularly on complexes of CDKs (CDK1, CDK2, CDK3, CDK4, CDK6, CDK7, CDK8 and CDK9) with their specific cyclines (A, B1, B2, C, D1, D2, D3, E, F, G1, G2, H, I and K) and viral cycline (cf. L. Mengtao in J. Virology 71(3), 1984–1991 (1997)), and the other compounds of the above general formula I wherein $R_1$ does not represent a hydrogen atom or a prodrug group, are valuable intermediate products for preparing the abovementioned compounds.

The present invention thus relates to the above compounds of general formula I, whilst the compounds wherein $R_1$ denotes a hydrogen atom or a prodrug group have valuable pharmacological properties, the pharmaceutical compositions containing the pharmacologically active compounds, their use and processes for preparing them.

In the above general formula I

X denotes an oxygen or sulphur atom, $R_1$ denotes a hydrogen atom, a $C_{1-4}$-alkoxy-carbonyl or $C_{2-4}$-alkanoyl group, $R_2$ denotes a carboxy or $C_{1-4}$-alkoxy-carbonyl group or an aminocarbonyl group optionally substituted by one or two $C_{1-3}$-alkyl groups, whilst the substituents may be identical or different, $R_3$ denotes a hydrogen atom or a $C_{1-6}$-alkyl group which may be substituted at the 2 position, in relation to the carbon atom of the $R_3$-C($R_4NR_5$)= group by a fluorine, chlorine or bromine atom, by a hydroxy, $C_{1-3}$-alkoxy, $C_{1-3}$-alkylsulphenyl, $C_{1-3}$-alkylsulphinyl, $C_{1-3}$-alkylsulphonyl, phenylsulphenyl, phenylsulphinyl, phenylsulphonyl, amino, $C_{1-3}$-alkylamino, di-($C_{1-3}$-alkyl)-amino, $C_{2-5}$-alkanoylamino or N-($C_{1-3}$-alkylamino)-$C_{2-5}$-alkanoylamino group, $R_4$ denotes a hydrogen atom, a $C_{1-6}$-alkyl group or a $C_{5-7}$-cycloalkyl group optionally substituted by a $C_{1-3}$-alkyl group wherein a methylene group in the 3 or 4 position in relation to the carbon atom of the $R_3$-C($R_4NR_5$)= group may be substituted by an imino group optionally substituted by a $C_{1-3}$-alkyl group, a phenyl or naphthyl group which may be substituted
by a fluorine, chlorine, bromine or iodine atom,
by a methoxy group optionally substituted by 1 to 3 fluorine atoms,
by a $C_{2-3}$-alkoxy which may be substituted in the 2 or 3 position by a $C_{1-3}$-alkylamino, di-($C_{1-3}$-alkyl)-amino or 5- to 7-membered cycloalkyleneimino group, whilst additionally an alkyl moiety in the abovementioned alkylamino and dialkylamino groups may be substituted by a phenyl group,
by a trifluoromethyl, amino, $C_{1-3}$-alkylamino, di-($C_{1-3}$-alkyl)-amino, $C_{2-5}$-alkanoylamino, N-($C_{1-3}$-alkyl)-$C_{2-5}$-alkanoylamino, $C_{1-5}$-alkylsulphonylamino, N-($C_{1-3}$-alkyl)-$C_{1-5}$-alkylsulphonylamino, phenylsulphonylamino, N-($C_{1-3}$-alkyl)-phenylsulphonylamino, aminosulphonyl, $C_{1-3}$-alkylaminosulphonyl or di-($C_{1-3}$-alkyl)-aminosulphonyl group, whilst additionally an alkyl moiety in the abovementioned alkylamino and dialkylamino groups may be substituted by a phenyl group,
by a carbonyl group which is substituted by a hydroxy, $C_{1-3}$-alkoxy, amino, $C_{1-3}$-alkylamino or N-($C_{1-5}$-alkyl)-$C_{1-3}$-alkylamino group, whilst additionally an alkyl moiety in the abovementioned groups may be substituted by a carboxy, $C_{1-3}$-alkoxycarbonyl or phenyl group or in the 2 or 3 position by a di-($C_{1-3}$-alkyl)-amino, piperazino, N-($C_{1-3}$-alkyl)-piperazino or 5- to 7-membered cycloalkyleneimino group,
by a $C_{1-3}$-alkyl group which is substituted by an amino, $C_{1-7}$-alkylamino, $C_{5-7}$-cycloalkylamino, $C_{5-7}$-cycloalkyl-$C_{1-3}$-alkylamino or phenyl-$C_{1-3}$-alkylamino group which may additionally be substituted at the amino nitrogen atom by a $C_{1-3}$-alkyl group wherein the hydrogen atoms are wholly or partially replaced by fluorine atoms, by a $C_{5-7}$-cycloalkyl, $C_{2-4}$-alkenyl or $C_{1-4}$-alkyl group, whilst the abovementioned $C_{1-4}$-alkyl substituent may in each case be additionally mono-, di- or trisubstituted by a cyano, carboxy, $C_{1-3}$-alkoxycarbonyl, pyridyl, imidazolyl, benzo[1,3]dioxole or phenyl group, wherein the phenyl group may be substituted by fluorine, chlorine or bromine atoms, by methyl, methoxy, trifluoromethyl, cyano or nitro groups and the substituents may be identical or different, or may be substituted in the 2, 3 or 4 position by a hydroxy group,
by a $C_{1-3}$-alkyl group which may be substituted by a hydroxy, carboxy, thiomorpholino, 1-oxido-thiomorpholino, 1,1-dioxido-thiomorpholino, piperazino, N-($C_{1-3}$-alkyl)-piperazino or N-phenyl-piperazino group, by a 5- to 7-membered cycloalkenyleneimino group or by a 4- to 7-membered cycloalkyleneimino group, wherein the abovementioned 5- to 7-membered cycloalkyleneimino groups may be substituted by one or two $C_{1-3}$-alkyl groups, by a $C_{5-7}$-cycloalkyl or phenyl group, by a $C_{1-3}$-alkyl, $C_{5-7}$-cycloalkyl, phenyl, carboxy or $C_{1-4}$-alkoxy-carbonyl group and by a hydroxy group and in the abovementioned cycloalkyleneimino groups a methylene group adjacent to the nitrogen atom may be replaced by a carbonyl group,
by a $C_{1-3}$-alkyl group which is substituted by a 5- to 7-membered cycloalkyleneimino group, whilst a phenyl group optionally mono- or disubstituted by fluorine, chlorine or bromine atoms or by methyl or methoxy groups, wherein the substituents may be identical or different, or an oxazolo, imidazolo, thiazolo, pyridino, pyrazino or pyrimidino group, optionally substituted by a fluorine, chlorine, bromine or iodine atom or by a methyl, methoxy or amino group, may be fused to the abovementioned 5- to 7-membered cycloalkyleneimino groups via two adjacent carbon atoms, whilst additionally the abovementioned monosubstituted phenyl groups may be substituted by a fluorine, chlorine or bromine atom or by a methyl, methoxy or nitro group, a 5-membered heteroaromatic group which contains an imino group, an oxygen or sulphur atom or an imino group, an oxygen or sulphur atom and one or two nitrogen atoms, or a 6-membered heteroaromatic group which contains one, two or three nitrogen atoms, whilst the abovementioned 5- and 6-membered heteroaromatic groups may additionally be substituted by a chlorine or bromine atom or by a methyl group, or a phenyl ring may be fused to the abovementioned 5- or 6-membered heteroaromatic groups via two adjacent carbon atoms, and $R_5$ denotes a hydrogen atom or a $C_{1-3}$-alkyl group.

Furthermore, the carboxy, amino or imino groups present in a compound of the above general formula I may be substituted by groups which can be cleaved in vivo.

In addition to the alkoxycarbonyl and alkanoyl groups already mentioned above, groups which can be cleaved in vivo include an acyl group such as the benzoyl, pyridinoyl, pentanoyl or hexanoyl group, an allyloxycarbonyl group, a $C_{1-16}$-alkoxycarbonyl group such as the pentoxycarbonyl, hexyloxycarbonyl, octyloxycarbonyl, nonyloxycarbonyl, decyloxycarbonyl, undecyloxycarbonyl, dodecyloxycarbonyl or hexadecyloxycarbonyl group, a phenyl-$C_{1-6}$-alkoxycarbonyl group such as the benzyloxycarbonyl, phenylethoxycarbonyl or phenylpropoxycarbonyl group, a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl or $R_cCO$—O—$(R_dCR_e)$—O—CO— group wherein $R_c$ denotes a $C_{1-8}$-alkyl, $C_{5-7}$-cycloalkyl, phenyl or phenyl-$C_{1-3}$-alkyl group, $R_e$ denotes a hydrogen atom, a $C_{1-3}$-alkyl, $C_{5-7}$-cycloalkyl or phenyl group and $R_d$ denotes a hydrogen atom or a $C_{1-3}$-alkyl group or the $R_cCO$—O—$(R_dCR_e)$—O— group, whilst the abovementioned ester groups may also be used as a group which can be converted in vivo into a carboxy group.

Preferred compounds of general formula I, however, are those wherein

X denotes an oxygen atom, $R_1$ denotes a hydrogen atom, $R_2$ denotes an aminocarbonyl group, $R_3$ denotes a hydrogen atom or a $C_{1-4}$-alkyl group which may be substituted, at the 2 position in relation to the carbon atom of the $R_3$-C($R_4NR_5$)= group by a chlorine or bromine atom or by a phenylsulphonyl group, $R_4$ denotes a hydrogen atom, a $C_{1-3}$-alkyl group or a cyclopentyl or cyclohexyl group optionally substituted by a methyl group, whilst in the cyclopentyl and cyclohexyl group a methylene group in the 3 or 4 position in relation to the carbon atom of the $R_3$-C($R_4NR_5$)= group may be replaced by an imino group optionally substituted by a methyl group, a phenyl group which is substituted
by a fluorine, chlorine, bromine or iodine atom,
by a methoxy group optionally substituted by 1 to 3 fluorine atoms,
by a $C_{2-3}$-alkoxy which is substituted in the 2 or 3 position by methylamino, dimethylamino or 5- to 7-membered cycloalkyleneimino group, whilst additionally a methyl group in the abovementioned amino groups may be substituted by a phenyl group,
by a trifluoromethyl, amino, $C_{2-5}$-alkanoylamino, N-($C_{1-3}$-alkyl)-$C_{2-5}$-alkanoylamino, $C_{1-5}$-alkylsulphonylamino, N-($C_{1-3}$-alkyl)-$C_{1-5}$-alkylsulphonylamino, phenylsulphonylamino, N-($C_{1-3}$-alkyl)-phenylsulphonylamino or aminosulphonyl group, whilst additionally an alkyl moiety in the abovementioned alkylamino and dialkylamino groups may be substituted by a phenyl group,
by a carbonyl group which is substituted by a hydroxy, $C_{1-3}$-alkoxy, amino, $C_{1-3}$-alkylamino or N-($C_{1-5}$-alkyl)-$C_{1-3}$-alkylamino group, whilst additionally an alkyl moiety in the abovementioned groups may be substituted by a carboxy, $C_{1-3}$-alkoxycarbonyl or phenyl group or in the 2 or 3 position by a di-($C_{1-3}$-alkyl)-amino, piperazino, N-($C_{1-3}$-alkyl)-piperazino or 5- to 7-membered cycloalkyleneimino group,
by a $C_{1-3}$-alkyl group which is substituted by an amino, $C_{1-7}$-alkylamino, $C_{5-7}$-cycloalkylamino, $C_{5-7}$-cycloalkyl-$C_{1-3}$-alkylamino or phenyl-$C_{1-3}$-alkylamino group which may additionally be substituted at the amino nitrogen atom by a $C_{1-3}$-alkyl group wherein the hydrogen atoms are wholly or partially replaced by fluorine atoms, by a $C_{5-7}$-cycloalkyl, $C_{2-4}$-alkenyl or $C_{1-4}$-alkyl group, whilst the abovementioned $C_{1-4}$-alkyl substituent may in each case be additionally substituted by a cyano, carboxy, $C_{1-3}$-alkoxycarbonyl, pyridyl, imidazolyl, benzo[1,3]dioxole or phenyl group, wherein the phenyl group may be monosubstituted by a fluorine, chlorine or bromine atom or by a methyl, methoxy, cyano, trifluoromethyl or nitro group, or di- or trisubstituted by fluorine, chlorine or bromine atoms or by methyl or methoxy groups, and the substituents may be identical or different, or may be substituted in the 2, 3 or 4 position by a hydroxy group,
by a $C_{1-3}$-alkyl group which may be substituted by a hydroxy, carboxy, thiomorpholino, 1-oxido-thiomorpholino, 1,1-dioxido-thiomorpholino, piperazino, N-($C_{1-3}$-alkyl)-piperazino or N-phenyl-piperazino group, by a 5- to 7-membered cycloalkenyleneimino group or by a 4- to 7-membered cycloalkyleneimino group, wherein the abovementioned 5- to 7-membered cycloalkyleneimino-groups may be substituted by one or two $C_{1-3}$-alkyl groups, by a cyclohexyl or phenyl group, by a $C_{1-3}$-alkyl, cyclohexyl, phenyl, carboxy or $C_{1-4}$-alkoxy-carbonyl group and by a hydroxy group and in the abovementioned cycloalkyleneimino groups a methylene group adjacent to the nitrogen atom may be replaced by a carbonyl group,
by a $C_{1-3}$-alkyl group which is substituted by a 5- to 7-membered cycloalkyleneimino group, whilst a phenyl group optionally mono- or disubstituted by fluorine, chlorine or bromine atoms or by methyl or methoxy groups, wherein the substituents may be identical or different, or a pyrazino or thiazolo group, optionally substituted by an amino group, may be fused to the abovementioned 5- to 7-membered cycloalkyleneimino groups via two adjacent carbon atoms, whilst additionally the abovementioned monosubstituted phenyl groups may be substituted by a fluorine, chlorine or bromine atom or by a methyl, methoxy or nitro group, a pyridyl group optionally substituted by a chlorine or bromine atom or by a methyl group, an oxazolyl, isoxazolyl, imidazolyl or thiazolyl group optionally substituted by a methyl group, to which a phenyl ring may be fused via two adjacent carbon atoms, and $R_5$ denotes a hydrogen atom or a $C_{1-3}$-alkyl group, particularly those compounds of general formula I wherein $R_1$ to $R_3$ and $R_5$ are as hereinbefore defined and $R_4$ denotes a hydrogen atom, a $C_{1-6}$-alkyl group or a $C_{5-7}$-cycloalkyl group optionally substituted by a $C_{1-3}$-alkyl group wherein a methylene group in the 3 or 4 position in relation to the carbon atom of the $R_3$-C$(R_4NR_5)$= group may be replaced by an imino group optionally substituted by a $C_{1-3}$-alkyl group, a phenyl or naphthyl group which may be substituted by a fluorine, chlorine or iodine atom, by a $C_{1-3}$-alkoxy, amino, $C_{1-3}$-alkylamino, di-($C_{1-3}$-alkyl)amino, $C_{2-5}$-alkanoylamino, N-($C_{1-3}$-alkylamino)-$C_{2-5}$-alkanoylamino, $C_{1-5}$-alkylsulphonylamino, N-($C_{1-3}$-alkyl)-$C_{1-5}$-alkylsulphonylamino, phenylsulphonylamino or N-($C_{1-3}$-alkyl)-phenylsulphonylamino group or by a $C_{1-3}$-alkyl group which may be substituted by a $C_{1-5}$-alkylamino, di-($C_{1-5}$-alkyl)-amino, thiomorpholino, 1-oxido-thiomorpholino, 1,1-dioxido-thiomorpholino, piperazino, N-($C_{1-3}$-alkyl)-piperazino, N-phenyl-piperazino, $C_{5-7}$-cycloalkenyleneimino group or by a $C_{4-7}$-cycloalkyleneimino group, whilst the abovementioned $C_{5-7}$-cycloalkyleneimino groups may be substituted by one or two $C_{1-3}$-alkyl groups, by a $C_{5-7}$-cycloalkyl or phenyl group, by a $C_{1-3}$-alkyl, $C_{5-7}$-cycloalkyl, phenyl, carboxy or $C_{1-4}$-alkoxycarbonyl group and by a hydroxy group, the isomers and salts thereof.

Particularly preferred compounds of general formula I are those wherein $R_1$ to $R_5$ are as hereinbefore defined and $R_2$ is in the 5 position, particularly those compounds wherein X denotes an oxygen atom, $R_1$ denotes a hydrogen atom, $R_2$ in the 5 position denotes an aminocarbonyl group, $R_3$ denotes a hydrogen atom or a $C_{1-4}$-alkyl group which may be terminally substituted by a chlorine or bromine atom or by a phenylsulphonyl group, $R_4$ denotes a hydrogen atom, a $C_{1-3}$-alkyl group or a cyclopentyl or cyclohexyl group optionally substituted by a methyl group, whilst in the cyclohexyl group a methylene group in the 4 position in relation to the carbon atom of the $R_3$-C$(R_4NR_5)$= group may be replaced by an imino group optionally substituted by a methyl group, a phenyl group which may be substituted by a fluorine, chlorine, bromine or iodine atom, by a methyl or ethyl group, which may in each case be substituted by a $C_{1-3}$-alkylamino, di-($C_{1-3}$-alkyl)-amino, thiomorpholino, 1-oxido-thiomorpholino, 1,1-dioxido-thiomorpholino, N-phenyl-piperazino, 5- to 6-membered cycloalkenyleneimino group or by a 5- to 7-membered cycloalkyleneimino group, whilst the abovementioned 5- to 7-membered cycloalkyleneimino groups may be substituted by one or two methyl groups, by a cyclohexyl or phenyl group, by a methyl, cyclohexyl or phenyl group and by a hydroxy group, or by a methyl or ethyl group which may be substituted by a phenyl group which is substituted by a 5 to 7-membered cycloalkyleneimino group, whilst additionally a phenyl ring is fused to the abovementioned cycloalkyleneimino groups via 2 adjacent carbon atoms, by a methyl or ethyl group substituted by an amino, methylamino or ethylamino group, each of which is additionally substituted at the amino nitrogen atom by a benzyl or phenylethyl group, wherein the phenyl moiety in the abovementioned groups may be monosubstituted by a fluorine, chlorine or bromine atom or by a methyl, methoxy, cyano, trifluoromethyl or nitro group or di- or trisubstituted by fluorine, chlorine or bromine atoms or by methyl or methoxy groups, and the substituents may be identical or different, whilst additionally the abovementioned monosubstituted phenyl groups may be substituted by a fluorine, chlorine or bromine atom or by a methyl, methoxy or nitro group, and $R_5$ denotes a hydrogen atom or a $C_{1-4}$-alkyl group, the isomers and the salts thereof.

Most particularly preferred compounds of general formula I are those wherein

X denotes an oxygen atom, $R_1$ denotes a hydrogen atom, $R_2$ in the 5 position denotes an aminocarbonyl group, $R_3$ denotes a hydrogen atom or a $C_{1-4}$-alkyl group, $R_4$ denotes a phenyl group which may be substituted by a fluorine, chlorine, bromine or iodine atom, by a methyl or ethyl group, which may be substituted in each case by a $C_{1-3}$-alkylamino, di-($C_{1-3}$-alkyl)-amino, thiomorpholino, 1-oxido-thiomorpholino, 1,1-dioxido-thiomorpholino, N-phenyl-piperazino, 5- to 6-membered cycloalkenyleneimino group or by a 5- to 7-membered cycloalkyleneimino group, whilst the abovementioned 5- to 7-membered cycloalkyleneimino groups may be substituted by one or two methyl groups, by a cyclohexyl or phenyl group, by a methyl, cyclohexyl or phenyl group and by a hydroxy group, or by a methyl or ethyl group which may be substituted by a phenyl group which is substituted in the 4 position by a 5 to 7-membered cycloalkyleneimino group, whilst additionally a phenyl ring is fused to the abovementioned cycloalkyleneimino groups via 2 adjacent carbon atoms, by a methyl or ethyl group substituted by an amino, methylamino or ethylamino group, each of which is additionally substituted at the amino nitrogen atom by a benzyl or phenylethyl group, and wherein the phenyl moiety may be monosubstituted by a fluorine, chlorine or bromine atom or by a methyl, methoxy, cyano, trifluoromethyl or nitro group, disubstituted by methyl or methoxy groups or trisubstituted by methyl or methoxy groups, and the substituents may be identical or different, whilst additionally the abovementioned monosubstituted phenyl groups may be substituted by a fluorine, chlorine or bromine atom or by a methyl, methoxy or nitro group, and $R_5$ denotes a hydrogen atom or a $C_{1-4}$-alkyl group, the isomers and the salts thereof.

The following are mentioned as examples of particularly preferred compounds:

(a) 3-Z-[1-(4-piperidinomethyl-phenylamino)-1-methyl-methylene]-5-amido-2-indolinone,
(b) 3-Z-[1-(4-bromo-phenylamino)-1-methyl-methylene]-5-amido-2-indolinone,
(c) 3-Z-[1-(4-piperidinomethyl-phenylamino)-1-butyl-methylene]-5-amido-2-indolinone,
(d) 3-Z-[1-(4-chlorophenylamino)-1-methyl-methylene]-5-amido-2-indolinone and
(e) 3-Z-(1-phenylamino-methylene)-5-amido-2-indolinone
(f) 3-Z-[1-(4-(N-benzyl-N-methyl-aminomethyl)-phenylamino)-1-methyl-methylene]-5-amido-2-indolinone,
(g) 3-Z-[1-(4-(N-(4-chlorobenzyl)-aminomethyl)-phenylamino)-1-methyl-methylene]-5-amido-2-indolinone,
(h) 3-Z-[1-(4-(N-benzyl-N-ethyl-aminomethyl)-phenylamino]-1-methyl-methylene]-5-amido-2-indolinone,
(i) 3-Z-[1-(4-(N-benzyl-aminomethyl)-phenylamino)-1-methyl-methylene]-5-amido-2-indolinone,
(j) 3-Z-[1-(4-(N-benzyl-N-methyl-aminomethyl)-phenylamino)-methylene]-5-amido-2-indolinone,
(k) 3-Z-[1-(4-(2,3,4,5-tetrahydro-benzo(d)azepin-3-yl-methyl)-phenylamino)-1-methyl-methylene]-5-amido-2-indolinone,
(l) 3-Z-[1-(4-piperidinomethyl-3-nitro-phenylamino)-1-methyl-methylene]-5-amido-2-indolinone and
(m) 3-Z-[1-(4-methyl-3-nitro-phenylamino)-1-methyl-methylene)-5-amido-2-indolinone
as well as the isomers and the salts thereof.

According to the invention, the new compounds may be obtained, for example, according to the following processes known in principle from the literature:

a. reacting a compound of general formula

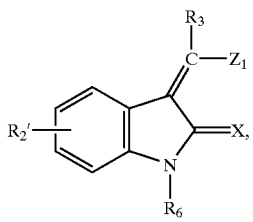

(II)

wherein
X and $R_3$ are as hereinbefore defined,
$R_2'$ has the meanings given for $R_2$ hereinbefore,
$R_6$ denotes a hydrogen atom or a protecting group for the nitrogen atom of the lactam group, whilst one of the groups $R_2'$ or $R_6$ may also denote a bond to a solid phase optionally formed via a spacer and the other group $R_2'$ or $R_6$ is as hereinbefore defined, and $Z_1$ denotes a halogen atom, a hydroxy, alkoxy or aralkoxy group, e.g. a chlorine or bromine atom or a methoxy, ethoxy or benzyloxy group, with an amine of general formula

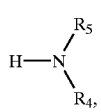

(III)

wherein
$R_4$ and $R_5$ are as hereinbefore defined,
and if necessary subsequently cleaving any protecting groups used for the nitrogen atom of the lactam group or from a solid phase.

A suitable protecting group for the nitrogen atom of the lactam group might be, for example, an acetyl, benzoyl, ethoxycarbonyl, tert.butyloxycarbonyl or benzyloxycarbonyl group and A suitable solid phase might be, for example, a resin such as a 4-(2', 4'-dimethoxyphenylaminomethyl)-phenoxy resin, the bonding preferably taking place via the amino group, or a p-benzyloxybenzylalcohol resin, the bonding preferably taking place via an intermediate member such as a 2,5-dimethoxy-4-hydroxy-benzyl derivative.

The reaction is appropriately carried out in a solvent such as dimethylformamide, toluene, acetonitrile, tetrahydrofuran, dimethylsulphoxide, methylene chloride or mixtures thereof, optionally in the presence of an inert base such as triethylamine, N-ethyl-diisopropylamine or sodium hydrogen carbonate at temperatures between 20 and 175° C., whilst any protecting group used may be cleaved at the same time as a result of transamidation.

If $Z_1$ in a compound of general formula II denotes a halogen atom, the reaction is preferably carried out in the presence of an inert base at temperatures of between 20 and 120° C.

If $Z_1$ in a compound of general formula II denotes a hydroxy, alkoxy or aralkoxy group, the reaction is preferably carried out at temperatures between 20 and 200° C.

The subsequent cleaving of any protecting group used, if necessary, is appropriately carried out either hydrolytically in an aqueous or alcoholic solvent, e.g. in methanol/water, ethanol/water, isopropanol/water, tetrahydrofuran/water, dioxan/water, dimethylformamide/water, methanol or ethanol in the presence of an alkali metal base such as lithium hydroxide, sodium hydroxide or potassium hydroxide at temperatures between 0 and 100° C., preferably at temperatures between 10 and 50° C., or more advantageously by transamidation with an organic base such as ammonia, methylamine, butylamine, dimethylamine or piperidine in a solvent such as methanol, ethanol, dimethylformamide and mixtures thereof or in an excess of the amine used, at temperatures of between 0 and 100° C., preferably at temperatures between 10 and 50° C.

Any solid phase used is preferably cleaved by means of trifluoroacetic acid and water at temperatures of between 0 and 35° C., preferably at ambient temperatures.

b. in order to prepare a compound of general formula I wherein $R_2$ denotes one of the abovementioned aminocarbonyl groups:

amidating a compound of general formula

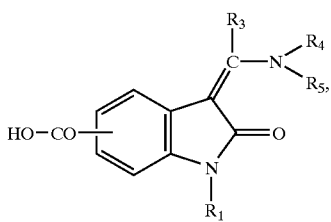

(IV)

wherein $R_1$ and $R_3$ are as hereinbefore defined, or the reactive derivatives thereof, with an amine of general formula

H—($R_7NR_8$) (V)

wherein $R_7$ and $R_8$ which may be identical or different denote hydrogen atoms or $C_{1-3}$-alkyl groups.

The amidation is preferably carried out in a solvent such as methylene chloride, diethyl ether, tetrahydrofuran, toluene, dioxan, acetonitrile, dimethylsulphoxide or dimethylformamide, optionally in the presence of an inorganic or tertiary organic base, preferably at temperatures between 20° C. and the boiling temperature of the solvent used. The amidation is carried out with a corresponding acid, preferably in the presence of a dehydrating agent, e.g. in the presence of isobutyl chloroformate, tetraethyl orthocarbonate, trimethyl orthoacetate, 2,2-dimethoxypropane, tetramethyloxysilane, thionylchloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxybenzotriazole, 2-(1H-benzotriazol-1-yl)-1,1,3,3-tetramethyluronium tetrafluoroborate, 2-(1H-benzotriazol-1-yl)-1,1,3,3-tetramethyluronium tetrafluoroborate/1-hydroxybenzotriazole, N,N'-carbonyldiimidazole or triphenylphosphine/carbon tetrachloride, and optionally with the addition of a base such as pyridine, 4-dimethylaminopyridine, N-methylmorpholine or triethylamine, appropriately at temperatures between 0 and 150° C., preferably at temperatures between 0 and 100° C., and the acylation is carried out with a corresponding reactive compound such as the anhydride, ester, imidazolide or halide thereof, optionally in the presence of a tertiary organic base such as triethylamine, N-ethyldiisopropylamine or N-methylmorpholine at temperatures between 0 and 150° C., preferably at temperatures between 50 and 100° C.

If according to the invention a compound of general formula I is obtained which contains an alkoxycarbonyl group, this may be converted by hydrolysis into a corresponding carboxy compound, or if a compound of general formula I is obtained which contains an amino or alkylamino group, this may be converted by alkylation or reductive alkylation into a corresponding alkylamino or dialkylamino compound, or if a compound of general formula I is obtained which contains an amino or alkylamino group, this may be converted by acylation into a corresponding acyl compound, or if a compound of general formula I is obtained which contains a carboxy group, this may be converted by esterification or amidation into a corresponding ester or aminocarbonyl compound, or if a compound of general formula I is obtained which contains a nitro group, this may be converted by reduction into a corresponding amino compound.

The subsequent hydrolysis is preferably carried out in an aqueous solvent, e.g. in water, isopropanol/water, tetrahydrofuran/water or dioxan/water, in the presence of an acid such as trifluoroacetic acid, hydrochloric acid or sulphuric acid or in the presence of an alkali metal base such as lithium hydroxide, sodium hydroxide or potassium hydroxide at temperatures between 0 and 100° C., preferably at temperatures between 10 and 50° C.

The subsequent reductive alkylation is preferably carried out in a suitable solvent such as methanol, methanol/water, methanol/water/ammonia, ethanol ether, tetrahydrofuran, dioxan or dimethylformamide, optionally with the addition of an acid such as hydrochloric acid in the presence of catalytically activated hydrogen, e.g. hydrogen in the presence of Raney nickel, platinum or palladium/charcoal, or in the presence of a metal hydride such as sodium borohydride, lithium borohydride or lithium aluminium hydride at temperatures between 0 and 100° C., preferably at temperatures between 20 and 80° C.

The subsequent alkylation is carried out with an alkylating agent such as an alkyl halide or dialkylsulphate such as methyl iodide, dimethylsulphate or propyl bromide, preferably in a solvent such as methanol, ethanol, methylene chloride, tetrahydrofuran, toluene, dioxan, dimethylsulphoxide or dimethylformamide, optionally in the presence of an inorganic or tertiary organic base such as triethylamine, N-ethyldiisopropylamine or dimethylaminopyridine, preferably at temperatures between 20° C. and the boiling temperature of the solvent used.

The subsequent acylation is preferably carried out in a solvent such as methylene chloride, diethyl ether, tetrahydrofuran, toluene, dioxan, acetonitrile, dimethylsulphoxide or dimethyl formamide, optionally in the presence of an inorganic or tertiary organic base, preferably at temperatures between 20° C. and the boiling temperature of the solvent used. The acylation is carried out with a corresponding acid, preferably in the presence of a dehydrating agent, e.g. in the presence of isobutyl chloroformate, tetraethyl orthocarbonate, trimethyl orthoacetate, 2,2-dimethoxypropane, tetramethoxysilane, thionylchloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxybenzotriazole, 2-(1H-benzotriazol-1-yl)-1,1,3,3-tetramethyluronium tetrafluoroborate, 2-(1H-benzotriazol-1-yl)-1,1,3,3-tetramethyluronium tetrafluoroborate/1-hydroxybenzotriazole, N,N'-carbonyldiimidazole or triphenylphosphine/carbon tetrachloride, and optionally with the addition of a base such as pyridine, 4-dimethylamino-pyridine, N-methylmorpholine or triethylamine, appropriately at temperatures of between 0 and 150° C., preferably at temperatures of between 0 and 100° C., and the acylation is carried out with a corresponding reactive compound such as an anhydride, ester, imidazole or halide thereof, optionally in the presence of a tertiary organic base such as triethylamine, N-ethyl-diisopropylamine or N-methyl-morpholine at temperatures of between 0 and 150° C., preferably at temperatures of between 50 and 100 C.

The subsequent esterification or amidation is appropriately carried out by reacting a corresponding reactive carboxylic acid derivative with a corresponding alcohol or amine as described hereinbefore.

The subsequent reduction of a nitro group is preferably carried out by hydrogenolysis, e.g. with hydrogen in the presence of a catalyst such as palladium/charcoal or Raney nickel in a solvent such as methanol, ethanol, ethyl acetate, dimethylformamide, dimethylformamide/acetone or glacial acetic acid, optionally with the addition of an acid such as hydrochloric acid or glacial acetic acid at temperatures between 0 and 50° C., but preferably at ambient temperature, and at a hydrogen pressure of from 1 to 7 bar, but preferably from 3 to 5 bar.

In the reactions described hereinbefore, any reactive groups present such as carboxy, amino, alkylamino or imino groups may be protected during the reaction by conventional protecting groups which are cleaved again after the reaction.

For example, a protecting group for a carboxy group may be a trimethylsilyl, methyl, ethyl, tert.butyl, benzyl or tetrahydropyranyl group and protecting groups for an amino, alkylamino or imino group may be an acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, tetrahydrofuran/water or dioxan/water, in the presence of an acid such as trifluoroacetic acid, hydrochloric acid or sulphuric acid or in the presence of an alkali metal base such as lithium hydroxide, sodium- hydroxide or potassium hydroxide, at temperatures between 0 and 100° C., preferably at temperatures between 10 and 50° C.

However, a benzyl, methoxybenzyl or benzyloxycarbonyl group is cleaved, for example hydrogenolytically, e.g. with hydrogen in the presence of a catalyst such as palladium/charcoal in a suitable solvent such as methanol, ethanol, ethyl acetate, dimethylformamide, dimethylformamide/acetone or glacial acetic acid, optionally with the addition of an acid such as hydrochloric acid or glacial acetic acid at temperatures between 0 and 50° C., but preferably at ambient temperature, and at a hydrogen pressure of 1 to 7 bar, but preferably 3 to 5 bar.

A methoxybenzyl group may also be cleaved in the presence of an oxidising agent such as cerium(IV) ammonium nitrate in a solvent such as methylene chloride, acetonitrile or acetonitrile/water at temperatures of between 0 and 50° C., preferably at ambient temperature.

A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid, optionally using a solvent such as methylene chloride, dioxan, ethyl acetate or ether.

A phthalyl group is preferably cleaved in the presence of hydrazine or a primary amine such as methylamine, ethylamine or n-butylamine in a solvent such as methanol, ethanol, isopropanol, toluene/water or dioxan at temperatures between 20 and 50° C.

Moreover, chiral compounds of general formula I obtained may be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid, N-acetylaspartic acid or quinic acid. An optically active alcohol may be for example (+) or (−)-menthol and an optically active acyl group in amides, for example, may be a (+)- or (−)-menthyloxycarbonyl group.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid, maleic or methanesulphonic acid.

Moreover, if the new compounds of formula I contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, arginine, cyclohexylamine, ethanolamine, diethanolamine and triethanolamine.

The compounds of general formulae I to V used as starting materials are known from the literature in some cases or are described in the Examples.

As already mentioned, the new compounds of general formula I wherein $R_1$ denotes a hydrogen atom or a prodrug group have valuable pharmacological properties, particularly an inhibitory effect on various kinases and cycline/CDK complexes, on the proliferation of cultivated human tumour cells and, when administered orally, on the growth of tumours in nude mice which have been infected with human tumour cells.

For example, the compounds listed in Table 1 were tested for their biological properties as follows:

Test 1

Inhibition of Cycline/CDK Enzyme, in vitro Activity

High Five™ insect cells (BTI-TN-5B1-4) which had been infected with a high titre of recombinant baculovirus were used to produce active human cycline/CDK holoenzymes. By using a baculovirus vector which contained two promoters (polyhedrin enhancer promoter, P10 enhancer promoter), GST-tagged cyclines (e.g. cycline D1 or cycline D3) with the corresponding $His_6$-tagged CDK subunit (e.g. for CDK4 or CDK6) were expressed in the same cell. The active holoenzyme was isolated by affinity chromatography on glutathione sepharose. Recombinant GST-tagged pRB (aa 379–928) was produced in *E. coli* and purified by affinity chromatography on glutathione sepharose.

The substrates used for the kinase assays depended on the specific kinases. Histone H1 (Sigma) was used as the substrate for cycline E/CDK2, cycline A/CDK2, cycline B/CDK1 and for v-cycline/CDK6. GST-tagged pRB (aa 379–928) was used as substrate for cycline D1/CDK4, cycline D3/CDK4, cycline D1/CDK6 and for cycline D3C/DK6.

Lysates of the insect cells infected with recombinant baculovirus or recombinant kinases (obtained from the lysates by purification) were incubated together with radio-labelled ATP in the presence of a suitable substrate with various concentrations of the inhibitor in a 1% DMSO (dimethyl sulphoxide) solution for 45 minutes at 30° C. The substrate proteins with associated radioactivity were precipitated with 5% TCA (trichloroacetic acid) in water-repellent PVDF multi-well microtitre plates (Millipore) or with 0.5% phosphoric acid solution on Whatman P81 filters. After the addition of scintillation liquid the radioactivity was measured in a Wallace 1450 Microbeta Liquid Scintillation Counter. For each concentration of the substance double measurements were carried out; $IC_{50}$ values were calculated for the enzyme inhibition.

Test 2

Inhibition of the Proliferation of Cultivated Human Tumour Cells

Cells of the Leiomyosarcoma tumour cell line SK-UT-1B (obtained from the American Type Culture Collection (ATCC)) were cultivated in Minimum Essential Medium with non-essential amino acids (Gibco), supplemented with sodium pyruvate (1 mmol), glutamine (2 mmol) and 10% foetal calf serum (Gibco) and harvested during the log-growth phase. Then the SK-UT-1B cells were added to Cytostar® multi-well plates (Amersham) at a density of 4000 cells per well and incubated overnight in an incubator. Various concentrations of the compounds (dissolved in DMSO; final concentration: <1%) were added to the cells. After 48 hours' incubation $^{14}$C-thymidine (Amersham) was added to each well and incubation was continued for a further 24 hours. The quantity of $^{14}$C-thymidine incorporated into the tumour cells in the presence of the inhibitor and representing the number of cells in the S phase was measured in a Wallace 1450 Microbeta Liquid Scintillation Counter. $IC_{50}$ values for the inhibition of proliferation (=inhibition of incorporated $^{14}$C-thymidine) were calculated, correcting for the background radiation. All the measurements were done twice.

Test 3

In Vivo Effects on Tumour-bearing Nude Mice $10^6$ cells [SK-UT-1B, or non-small cell lung tumour NCI-H460 (obtained from ATCC)] in a volume of 0.1 ml were injected subcutaneously into male and/or female nude mice (NMRI nu/nu; 25–35 g; N=10–20); alternatively, small fragments of SK-UT-1B or NCI-H460 cell clumps were implanted subcutaneously. One to three weeks after the injection or implantation a kinase inhibitor was administered daily by oral route for a period of 2 to 4 weeks (by oesophageal tube). The size of the tumour was measured three times a week using a digital sliding gauge. The effect of a kinase inhibitor on the tumour growth was determined as a percentage inhibition compared with a control group treated with placebo.

Table 2 which follows contains the results obtained in in vitro test 2:

| Compound (example no.) | Inhibition of SKUT −1B proliferation $IC_{50}$ [:M] |
|---|---|
| 1(11) | 0.032 |
| 1(8) | 0.060 |
| 1(26) | 0.036 |
| 1(3) | 0.040 |
| 1(1) | 0.100 |
| 1(96) | 0.005 |
| 1(91) | 0.010 |
| 1(95) | 0.008 |
| 1(51) | 0.013 |
| 1(105) | 0.019 |
| 1(110) | 0.020 |
| 1(117) | 0.020 |
| 1(71) | 0.030 |

In view of their biological properties, the new compounds of general formula I, their isomers and physiologically acceptable salts are suitable for the treatment of diseases characterised by excessive or abnormal cell proliferation.

Such diseases include (with no claim to completeness): viral infections (e.g. HIV and Kaposi's sarcoma); inflammation and autoimmune diseases (e.g. colitis, arthritis, Alzheimer's disease, glomerulonephritis and wound healing); bacterial, fungal and/or parasitic infections; leukaemias, lymphoma and solid tumours; skin diseases (e.g. psoriasis); bone diseases; cardiovascular diseases (e.g. restenosis and hypertrophy).

They are also useful for protecting proliferating cells (e.g. hair, intestinal, blood and progenitor cells) against DNA damage caused by radiation, UV treatment and/or cytostatic treatment.

The new compounds may be used for the short-term or long-term treatment of the abovementioned diseases, optionally in conjunction with other 'state of the art' compounds such as other cytostatics.

The dosage required to achieve such an effect is appropriately 0.1 to 30 mg/kg, preferably 0.3 to 10 mg/kg by intravenous route, and 0.1 to 100 mg/kg, preferably 0.3 to 30 mg/kg by oral route, in each case administered 1 to 4 times a day. For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The Examples which follow are intended to illustrate the invention:

EXAMPLE I

Methyl 1-acetyl-2-indolinone-5-carboxylate 10.5 g of methyl 2-indolinone-5-carboxylate (prepared analogously to Ogawa, Hidenori et al. in Chem.Pharm.Bull 36, 2253–2258 (1988)) are stirred in 30 ml of acetic anhydride for 4 hours at 140° C. The mixture is then left to cool, poured onto ice water and the precipitate is suction filtered. The product is washed with water once more, then taken up in methylene chloride, dried over sodium sulphate and concentrated by evaporation.

Yield: 11 g (86% of theory), $R_f$ value: 0.63 (silica gel, methylene chloride/methanol= 50:1)

EXAMPLE II

Methyl 1-acetyl-3-(1-ethoxy-1-butyl-methylene]-2-indolinone-5-carboxylate 11 g of methyl 1-acetyl-2-indolinone-5-carboxylate are stirred in 110 ml of acetic anhydride and 30 ml of triethyl orthovalerate for 2 hours at 100° C. Then it is concentrated by rotary evaporation, the residue is washed with ether and suction filtered.

Yield: 11.5 g (67% of theory), $R_f$ value: 0.55 (silica gel, methylene chloride/petroleum etherethyl acetate=4:5:1)

The following compounds are prepared analogously to Example II:

(1) methyl 1-acetyl-3-(1-ethoxy-methylene]-2-indolinone-5-carboxylate Prepared from methyl 1-acetyl-2-indolinone-5-carboxylate and trimethyl orthoformate
(2) methyl 1-acetyl-3-(1-ethoxy-1-methyl-methylene]-2-indolinone-5-carboxylate Prepared from methyl 1-acetyl-2-indolinone-5-carboxylate and triethyl orthoacetate
(3) methyl 1-acetyl-3-(1-ethoxy-1-ethyl-methylene]-2-indolinone-5-carboxylate Prepared from methyl 1-acetyl-2-indolinone-5-carboxylate and triethyl orthopropionate

EXAMPLE III 28.0 g of Rink resin (MBHA resin made by Novobiochem) were allowed to swell in 330 m of dimethylformamide. Then 330 ml of 30% piperidine in dimethyl formamide were added and the mixture was shaken for 7 minutes to cleave the 9H-fluoren-9-yl-methoxycarbonyl group. Then the resin was washed several times with dimethylformamide. Finally, 7.3 g 10.5 g of 2-indolinone-5-carboxylic acid (prepared analogously to Ogawa, Hidenori et al., Chem. Pharm. Bull 36, 2253–2258 (1988)), 5.6 g of hydroxybenzotriazole, 13.3 g of O-(benzotriazol-1-yl)-N,N,N',N'-tetramethyluronium tetrafluoroborate and 5.7 ml of N-ethyl-diisopropylamine in 300 ml of dimethylformamide were added and the mixture was shaken for 1 hour. The solution was suction filtered and the resin was washed five times with 300 ml of dimethylformamide and three times with 300 ml of methylene chloride. To dry it, nitrogen was blown through the resin.

Yield: 20 g of charged resin

EXAMPLE IV 0.4 g of the charged resin prepared in Example III were stirred with 2.5 ml of acetic anhydride at 90° C. for 1 hour. Then 2.5 ml of trimethyl orthovalerate were added and the mixture was shaken for a further 3 hours at 110° C. Then the resin was suction filtered and washed with dimethylformamide, methanol and finally with methylene chloride.

Yield: 0.6 g of moist resin

The following charged resins were prepared analogously to Example IV:

(1) resin charged with 3-Z-(1-ethoxy-methylene)-5-amido-2-indolinone by reacting the product of Example I and triethyl orthoformate
(2) resin charged with 3-Z-(1-methoxy-1-methyl-methylene)-5-amido-2-indolinone by reacting the product of Example I and trimethyl orthoformate
(3) resin charged with 3-Z-(1-methoxy-1-ethyl-methylene)-5-amido-2-indolinone by reacting the product of Example I and trimethyl orthopropionate
(4) resin charged with 3-Z-(1-methoxy-1-propyl-methylene)-5-amido-2-indolinone by reacting the product of Example I and trimethyl orthobutyrate
(5) resin charged with 3-Z-(1-methoxy-1-ethenyl-methylene)-5-amido-2-indolinone by reacting the product of Example I and 3,3,3-triethoxyprop-1-ene
(6) resin charged with 3-Z-(1-methoxy-1-(3-bromo-propyl)-methylene)-5-amido-2-indolinone by reacting the product of Example I and trimethyl 4-bromo-orthobutyrate
(7) resin charged with 3-Z-(1-methoxy-1-(2-phenylsulphonyl-ethyl)-methylene)-5-amido-2-indolinone by reacting the product of Example I and triethyl 3-phenylsulphonyl-orthopropionate

EXAMPLE V 4-(N-Ethyl-aminomethyl)-nitrobenzene 6 g of 4-nitrobenzylbromide are dissolved in 25 ml of ethanol, mixed with 25 ml of 10% ethanolic ethylamine solution and refluxed for 2 hours. Then the solution is concentrated by rotary evporation, the residue is taken up in methylene chloride and washed with dilute sodium hydroxide solution. Then the organic phase is concentrated by evaporation.

Yield: 2.3 g (46% of theory), $R_f$ value: 0.20 (silica gel, methylene chloride/methanol= 9:1)

The following compounds are prepared analogously to Example V:

4-[N-(4-chlorophenyl-methyl)-aminomethyl]-nitrobenzene
4-(N-cyclohexyl-aminomethyl)-nitrobenzene
4-(N-isopropyl-aminomethyl)-nitrobenzene
4-(N-butyl-aminomethyl)-nitrobenzene
4-(N-methoxycarbonylmethyl-aminomethyl)-nitrobenzene
4-(N-benzyl-aminomethyl)-nitrobenzene
4-(pyrrolidino-methyl)-nitrobenzene
4-(morpholino-methyl)-nitrobenzene
4-(piperidino-methyl)-nitrobenzene.
4-(hexamethyleneimino-methyl)-nitrobenzene
4-(4-hydroxy-piperidino-methyl)-nitrobenzene
4-(4-methyl-piperidino-methyl)-nitrobenzene
4-(4-ethyl-piperidino-methyl)-nitrobenzene
4-(4-isopropyl-piperidino-methyl)-nitrobenzene
4-(4-phenyl-piperidino-methyl)-nitrobenzene
4-(4-benzyl-piperidino-methyl)-nitrobenzene
4-(4-ethoxycarbonyl-piperidino-methyl)-nitrobenzene
4-(dimethylamino-methyl)-nitrobenzene
4-(di-n-propylamino-methyl)-nitrobenzene
4-(4-tert.butoxycarbonyl-piperazino-methyl)-nitrobenzene
3-(dimethylamino-methyl)-nitrobenzene
4-(2-diethylamino-ethyl)-nitrobenzene
4-(2-morpholino-ethyl)-nitrobenzene
4-(2-pyrrolidino-ethyl)-nitrobenzene
4-(2-piperidino-ethyl)-nitrobenzene
4-(N-ethyl-N-benzyl-aminomethyl)-nitrobenzene 4-(N-n-propyl-N-benzyl-aminomethyl)-nitrobenzene
4-[N-methyl-N-(4-chlorophenylmethyl)-aminomethyl]-nitrobenzene
4-[N-methyl-N-(4-bromophenylmethyl)-aminomethyl]-nitrobenzene
4-[N-methyl-N-(3-chlorophenylmethyl)-aminomethyl]-nitrobenzene
4-[N-methyl-N-(3,4-dimethoxyphenylmethyl)-aminomethyl]-nitrobenzene
4-[N-methyl-N-(4-methoxyphenylmethyl)-aminomethyl]-nitrobenzene
4-[N-(2,2,2-trifluoroethyl)-N-benzyl-aminomethyl]-nitrobenzene
4-[N-(2,2,2-trifluoroethyl)-N-(4-chlorophenylmethyl)-aminomethyl]-nitrobenzene
4-(2,6-dimethyl-piperidino-methyl)-nitrobenzene
4-(thiomorpholino-methyl)-nitrobenzene
4-(S-oxido-thiomorpholino-methyl)-nitrobenzene
4-(S,S-dioxido-thiomorpholino-methyl)-nitrobenzene
4-(azetidino-methyl)-nitrobenzene
4-(2,5-dihydropyrrol-1-yl-methyl)-nitrobenzene
4-(3,6-dihydro-2H-pyridin-1-yl-methyl)-nitrobenzene
4-(2-methoxycarbonyl-pyrrolidino-methyl)-nitrobenzene
4-(3,5-dimethyl-piperidino-methyl)-nitrobenzene
4-(4-phenyl-piperazinyl-methyl)-nitrobenzene
4-(4-phenyl-4-hydroxy-piperidino-methyl)-nitrobenzene
4-[N-(3,4,5-trimethoxy-benzyl)-N-methyl-aminomethyl]-nitrobenzene
4-[N-(3,4-dimethoxy-benzyl)-N-ethyl-aminomethyl]-nitrobenzene
4-[N-(3-chlorobenzyl)-N-methyl-aminomethyl]-nitrobenzene
4-[N-(2,6-dichlorobenzyl)-N-methyl-aminomethyl]-nitrobenzene
4-[N-(4-trifluoromethylbenzyl)-N-methyl-aminomethyl]-nitrobenzene
4-(N-benzyl-N-isopropyl-aminomethyl)-nitrobenzene
4-(N-benzyl-N-tert.butyl-aminomethyl)-nitrobenzene
4-(diisopropylamino-methyl)-nitrobenzene
4-(di-n-propylamino-methyl)-nitrobenzene
4-(diisobutylamino-methyl)-nitrobenzene
4-(2,3,4,5-tetrahydro-benzo(d)azepin-3-yl-methyl)-nitrobenzene
4-(2,3-dihydro-isoindol-2-yl-methyl)-nitrobenzene
4-(6,7-dimethoxy-1,2,3,4-tetrahydro-isoquinolin-2-yl-methyl)-nitrobenzene
4-(1,2,3,4-tetrahydro-isoquinolin-2-yl-methyl)-nitrobenzene
4-[N-(2-hydroxyethyl)-N-benzyl-aminomethyl]-nitrobenzene
4-[N-(1-ethyl-pentyl)-N-(pyridin-2-yl-methyl)-aminomethyl]-nitrobenzene
4-(N-phenethyl-N-methyl-aminomethyl)-nitrobenzene
4-[N-(3,4-dihydroxy-phenethyl)-N-methyl-aminomethyl]-nitrobenzene
4-[N-(3,4,5-trimethoxy-phenethyl)-N-methyl-aminomethyl]-nitrobenzene
4-[N-(3,4-dimethoxy-phenethyl)-N-methyl-aminomethyl]-nitrobenzene
4-[N-(4-nitro-phenethyl)-N-methyl-aminomethyl]-nitrobenzene
4-(N-phenethyl-N-benzyl-aminomethyl)-nitrobenzene
4-(N-phenethyl-N-cyclohexyl-aminomethyl)-nitrobenzene
4-[N-(2-(pyridin-2-yl)-ethyl)-N-methyl-aminomethyl]-nitrobenzene
4-[N-(2-(pyridin-4-yl)-ethyl)-N-methyl-aminomethyl]-nitrobenzene
4-[N-(pyridin-4-yl-methyl)-N-methyl-aminomethyl]-nitrobenzene
4-(dibenzylamino-methyl)-nitrobenzene
4-[N-(4-nitro-benzyl)-N-propyl-aminomethyl]-nitrobenzene
4-[N-benzyl-N-(3-cyano-propyl)-aminomethyl]-nitrobenzene
4-(N-benzyl-N-allyl-aminomethyl)-nitrobenzene
4-[N-(benzo( 1,3)dioxol-5-yl-methyl)-N-methyl-aminomethyl]-nitrobenzene
4-(7-chloro-2,3,4,5-tetrahydro-benzo(d)azepin-3-yl-methyl)-nitrobenzene
4-(7,8-dichloro-2,3,4,5-tetrahydro-benzo(d)azepin-3-yl-methyl)-nitrobenzene
4-(7-methoxy-2,3,4,5-tetrahydro-benzo(d)azepin-3-yl-methyl)-nitrobenzene
4-(7-methyl-2,3,4,5-tetrahydro-benzo(d)azepin-3-yl-methyl)-nitrobenzene
4-(7,8-dimethoxy-2,3,4,5-tetrahydro-benzo(d)azepin-3-yl-methyl)-nitrobenzene
4-(6,7-dichloro-1,2,3,4-tetrahydro-isoquinolin-2-yl-methyl)-nitrobenzene
4-(6,7-dimethyl-1,2,3,4-tetrahydro-isoquinolin-2-yl-methyl)-nitrobenzene
4-(6-chloro-1,2,3,4-tetrahydro-isoquinolin-2-yl-methyl)-nitrobenzene
4-(7-chloro-1,2,3,4-tetrahydro-isoquinolin-2-yl-methyl)-nitrobenzene
4-(6-methoxy-1,2,3,4-tetrahydro-isoquinolin-2-yl-methyl)-nitrobenzene
4-(7-methoxy-1,2,3,4-tetrahydro-isoquinolin-2-yl-methyl)-nitrobenzene
4-(2,3,4,5-tetrahydro-azepino(4,5-b)pyrazin-3-yl)-methyl)-nitrobenzene
4-(7-amino-2,3,4,5-tetrahydro-azepino(4,5-b)pyrazin-3-yl-methyl)-nitrobenzene
4-(2-amino-5,6,7,8-tetrahydro-azepino(4,5-d)thiazol-6-yl-methyl)-nitrobenzene
4-( 5,6,7,8-tetrahydro-azepino(4,5-d) thiazol-6- yl-methyl)-nitrobenzene

EXAMPLE VI 4-(N-Ethyl-N-tert.butoxycarbonyl-aminomethyl)-nitrobenzene 2.2 g of 4-(N-ethyl-aminomethyl)-nitrobenzene are dissolved in 50 ml of ethyl acetate and stirred with 2.6 g of di-tert.butyl-dicarbonate for 30 minutes at ambient temperature. Then the solution is washed with water and concentrated by evaporation.

Yield: 3.4 g (97% of theory), $R_f$ value: 0.90 (silica gel, methylene chloride/methanol=9:1)

The following compounds are prepared analogously to Example VI:

4-[N-(4-chlorophenylmethyl)-N-tert.butoxycarbonyl-aminomethyl]-nitrobenzene
4-(N-cyclohexyl-N-tert.butoxycarbonyl-aminomethyl)-nitrobenzene
4-(N-isopropyl-N-tert.butoxycarbonyl-aminomethyl)-nitrobenzene
4-(N-butyl-N-tert.butoxycarbonyl-aminomethyl)-nitrobenzene
4-(N-methoxycarbonylmethyl-N-tert.butoxycarbonyl-aminomethyl)-nitrobenzene 4-(N-benzyl-N-tert.butoxycarbonyl-aminomethyl)-nitrobenzene
4-(N-ethyl-N-tert.butoxycarbonyl-aminomethyl)-nitrobenzene

EXAMPLE VII 4-(N-Ethyl-N-tert.butoxycarbonyl-aminomethyl)-aniline 6.4 g of 4-(N-ethyl-N-tert.butoxycarbonyl-aminomethyl)-nitrobenzene are dissolved in 60 ml of methanol and hydrogenated with 1.5 g of Raney nickel at ambient temperature under 3 bar. The catalyst is then filtered off and the solution is evaporated down.

Yield: 4.78 g $R_f$ value: 0.70 (silica gel, methylene chloride/methanol=50:1)

The following compounds are prepared analogously to Example VII:

4-[N-(4-chlorophenylmethyl)-N-tert.butoxycarbonyl-aminomethyl)-aniline
4-(N-cyclohexyl-N-tert.butoxycarbonyl-aminomethyl)-aniline
4-(N-isopropyl-N-tert.butoxycarbonyl-aminomethyl)-aniline
4-(N-butyl-N-tert.butoxycarbonyl-aminomethyl)-aniline
4-(N-methoxycarbonylmethyl-N-tert.butoxycarbonyl-aminomethyl)-aniline
4-(N-benzyl-N-tert.butoxycarbonyl-aminomethyl)-aniline
4-(pyrrolidino-methyl)-aniline
4-(morpholino-methyl)-aniline
4-(piperidino-methyl)-aniline
4-(hexamethyleneimino-methyl)-aniline
4-(4-hydroxy-piperidino-methyl)-aniline
4-(4-methyl-piperidino-methyl)-aniline
4-(4-ethyl-piperidino-methyl)-aniline
4-(4-isopropyl-piperidino-methyl)-aniline
4-(4-phenyl-piperidino-methyl)-aniline
4-(4-benzyl-piperidino-methyl)-aniline
4-(4-ethoxycarbonyl-piperidino-methyl)-aniline
4-(dimethylamino-methyl)-aniline
4-(di-n-propylamino-methyl)-aniline
4-(4-tert.butoxycarbonyl-piperazino-methyl)-aniline
3-(dimethylamino-methyl)-aniline
4-(2-diethylamino-ethyl)-aniline
4-(2-morpholino-ethyl)-aniline
4-(2-pyrrolidino-ethyl)-aniline
4-(2-piperidino-ethyl)-aniline
4-(N-ethyl-N-benzyl-aminomethyl)-aniline
4-(N-propyl-N-benzyl-aminomethyl)-aniline
4-(N-methyl-N-(4-chlorophenylmethyl)-aminomethyl)-aniline
4-(N-methyl-N-(4-bromophenylmethyl)-aminomethyl)-aniline
4-(N-methyl-N-(3-chlorophenylmethyl)-aminomethyl)-aniline
4-(N-methyl-N-(3,4-dimethoxyphenylmethyl)-aminomethyl)-aniline
4-(N-methyl-N-(4-methoxyphenylmethyl)-aminomethyl)-aniline
4-[N-(2,2,2-trifluoroethyl)-N-benzyl-aminomethyl]-aniline
4-[N-(2,2,2-trifluoroethyl)-N-benzyl-aminomethyl)-aminomethyl]-aniline
4-(2,6-dimethyl-piperidino-methyl)-aniline
4-(thiomorpholino-methyl)-aniline
4-(S-oxido-thiomorpholino-methyl)-aniline
4-(S,S-dioxido-thiomorpholino-methyl)-aniline
4-(azetidino-methyl)-aniline
4-(2,5-dihydropyrrol-1-yl-methyl)-aniline
4-(3,6-dihydro-2H-pyridin-1-yl-methyl)-aniline
4-(2-methoxycarbonyl-pyrrolidino-methyl)-aniline
4-(3,5-dimethyl-piperidino-methyl)-aniline
4-(4-phenyl-piperazino-methyl)-aniline
4-(4-phenyl-4-hydroxy-piperidino-methyl)-aniline
4-[N-(3,4,5-trimethoxybenzyl)-N-methyl-aminomethyl]-aniline
4-[N-(3,4-dimethoxybenzyl)-N-ethyl-aminomethyl]-aniline
4-(N-benzyl-N-ethyl-aminomethyl)-aniline
4-[N-(3-chlorobenzyl)-N-methyl-aminomethyl]-aniline
4-[N-(2,6-dichlorobenzyl)-N-methyl-aminomethyl]-aniline
4-[N-(4-trifluoromethylbenzyl)-N-methyl-aminomethyl)-aniline
4-(N-benzyl-N-isopropyl-aminomethyl)-aniline
4-(N-benzyl-N-tert.butyl-aminomethyl)-aniline
4-(diisopropylamino-methyl)-aniline
4-(di-n-propylamino-methyl)-aniline
4-(diisobutylamino-methyl)-aniline
4-(2,3,4,5-tetrahydro-benzo(d)azepin-3-yl-methyl)-aniline
4-(2,3-dihydro-isoindol-2-yl-methyl)-aniline
4-(6,7-dimethoxy-1,2,3,4-tetrahydro-isoquinolin-2-yl-methyl)-aniline
4-(1,2,3,4-tetrahydro-isoquinolin-2-yl -methyl)-aniline
4-[N-(2-hydroxyethyl)-N-benzyl-aminomethyl]-aniline
4-[N-(1-ethyl-pentyl)-N-(pyridin-2-yl-methyl)-aminomethyl]-aniline
4-(N-phenethyl-N-methyl-aminomethyl)-aniline
4-(1,2,3,4-dihydroxy-phenethyl)-N-methyl-aminomethyl)-aniline
4-[N-(3,4,5-trimethoxy-phenethyl)-N-methyl-aminomethyl]-aniline
4-[N-(3,4-dimethoxy-phenethyl)-N-methyl-aminomethyl]-aniline
4-[N-(4-nitro-phenethyl)-N-methyl-aminomethyl]-aniline
4-(N-phenethyl-N-benzyl-aminomethyl)-aniline
4-(N-phenethyl-N-cyclohexyl-aminomethyl)-aniline
4-[N-(2-pyridin-2-yl)-ethyl)-N-methyl-aminomethyl]-aniline
4-[N-(2-(pyridin-4-yl)-ethyl)-N-methyl-aminomethyl]-aniline
4-[N-(pyridin-4-yl-methyl)-N-methyl-aminomethyl]-aniline
4-(dibenzylamino-methyl)-aniline
4-[N-(4-nitro-benzyl)-N-propyl-aminomethyl]-aniline
4-[N-benzyl-N-(3-cyano-propyl)-aminomethyl)-aniline
4-(N-benzyl-N-allyl-aminomethyl)-aniline
4-[N-benzyl-N-(2,2,2-trifluoroethyl)-aminomethyl]-aniline
4-[N-(benzo(1,3)dioxol-5-yl-methyl)-N-methyl-aminomethyl]-aniline
4-(7-chloro-2,3,4,5-tetrahydro-benzo(d)azepin-3-yl-methyl)-aniline
4-(7,8-dichloro-2,3,4,5-tetrahydro-benzo(d)azepin-3-yl-methyl)-aniline
4-(7-methoxy-2,3,4,5-tetrahydro-benzo(d)azepin-3-yl-methyl)-aniline
4-(7-methyl-2,3,4,5-tetrahydro-benzo(d)azepin-3-yl-methyl)-aniline
4-(7,8-dimethoxy-2,3,4,5-tetrahydro-benzo(d)azepin-3-yl-methyl)-aniline
4-(6,7-dichloro-1,2,3,4-tetrahydro-isoquinolin-2-yl-methyl)-aniline
4-(6,7-dimethyl-1,2,3,4-tetrahydro-isoquinolin-2-yl-methyl)-aniline
4-(6-chloro-1,2,3,4-tetrahydro-isoquinolin-2-yl-methyl)-aniline 4-(7-chloro-1,2,3,4-tetrahydro-isoquinolin-2-yl-methyl)-aniline 4-(6-methoxy-1,2,3,4-tetrahydro-isoquinolin-2-yl-methyl)-aniline 4-(7-methoxy-1,2,3,4-tetrahydro-isoquinolin-2-yl-methyl)-aniline 4-(2,3,4,5-tetrahydro-azepino(4,5-b)pyrazin-3-yl-methyl)-aniline 4-(7-amino-2,3,4,5-tetrahydro-azepino(4,5-b)pyrazin-3-yl-methyl)-aniline 4-(2-amino-5,6,7,8-tetrahydro-azepino(4,5-d)thiazol-6-yl-methyl)-aniline 4-(5,6,7,8-tetrahydro-azepino(4,5-d)thiazol-6-yl-methyl)-aniline Preparation of the end products:

EXAMPLE 1

BIBE 1790

3-Z-(1-phenylamino-1-butyl-methylene)-5-amido-2-indolinone 600 g of a resin prepared according to Example IV were suspended in 3 ml of dimethylformamide and shaken with 0.4 g of aniline for 10 hours at 70° C. Then the mixture was filtered and the resin was washed several times with methylene chloride, methanol and dimethylformamide. Then 3 ml of methanolic ammonia were added for 2 hours in order to cleave the acetyl group. Finally, after further washing with dimethylformamide and methylene chloride, 4 ml of 10% trifluoroacetic acid in methylene chloride were added over 90 minutes, the resin was separated off and the solution was concentrated by evaporation. The residue was taken up in a little 1N sodium hydroxide solution and extracted with a little methylene chloride. The organic phase was dried over sodium sulphate and concentrated by rotary evaporation.

Yield: 37 mg $R_f$ value: 0.6 (silica gel, methylene chloride/methanol= 9:1)

$C_{20}H_{21}N_3O_2$ mass spectrum: m/z=335 ($M^+$)

The following compounds are prepared analogously to Example 1:

(1) 3-Z-(1-phenylamino-methylene)-5-amido-2-indolinone

Prepared from the resin prepared according to Example IV(1) and aniline $R_f$ value: 0.59 (silica gel, methylene chloride/methanol= 9:1)

$C_{16}H_{13}N_3O_2$ mass spectrum: m/z=279 ($M^+$)

(2) 3-Z-[1-(4-methyl-phenylamino)-1-methyl-methylene]-5-amido-2-indolinone

Prepared from the resin according to Example IV(2) and 4-methylaniline $R_f$ value: 0.44 (silica gel, methylene chloride/methanol= 9:1)

$C_{18}H_{17}N_3O_2$ mass spectrum: m/z=307 ($M^+$)

(3) 3-Z-[1-(4-Chloro-phenylamino)-1-methyl-methylene]-5-amido-2-indolinone

Prepared from the resin according to Example IV(2) and 4-chloroaniline $R_f$ value: 0,45 (silica gel, methylene chloride/methanol= 9:1)

$C_{17}H_{14}ClN_3O_2$ mass spectrum: m/z=327/329 ($M^+$)

(4) 3-Z-[1-(4-ethyl-phenylamino)-1-methyl-methylene]-5-amido-2-indolinone

Prepared from the resin according to Example IV(2) and 4-ethylaniline $R_f$ value: 0.43 (silica gel, methylene chloride/methanol= 9:1)

$C_{19}H_{19}N_3O_2$ mass spectrum: m/z=321 ($M^+$)

(5) 3-Z-[1-(4-methoxy-phenylamino)-1-methyl-methylene]-5-amido-2-indolinone

Prepared from the resin according to Example IV(2) and 4-methoxyaniline $R_f$ value: 0.46 (silica gel, methylene chloride/methanol= 9:1)

$C_{18}H_{17}N_3O_3$ mass spectrum: m/z=323 ($M^+$)

(6) 3-Z-[1-(4-iodo-phenylamino)-1-methyl-methylene]-5-amido-2-indolinone

Prepared from the resin according to Example IV(2) and 4-iodoaniline $R_f$ value: 0.36 (silica gel, methylene chloride/methanol= 9:1)

$C_{17}H_{14}IN_3O_2$ mass spectrum: m/z=419 ($M^+$)

(7) 3-Z-[1-(4-fluoro-phenylamino)-1-methyl-methylene]-5-amido-2-indolinone

Prepared from the resin according to Example IV(2) and 4-fluoroaniline $R_f$ value: 0.60 (silica gel, methylene chloride/methanol= 9:1)

$C_{17}H_{14}FN_3O_2$ mass spectrum: m/z=311 ($M^+$)

(8) 3-Z-[1-(4-bromo-phenylamino)-1-methyl-methylene]-5-amido-2-indolinone

Prepared from the resin according to Example IV(2) and 4-bromoaniline $R_f$ value: 0.53 (silica gel, methylene chloride/methanol= 9:1)

$C_{17}H_{14}BrN_3O_2$ mass spectrum: m/z=371/373 ($M^+$)

(9) 3-Z-(1-phenylamino-1-methyl-methylene)-5-amido-2-indolinone

Prepared from the resin according to Example IV(2) and aniline $R_f$ value: 0,58 (silica gel, methylene chloride/methanol= 9:1)

$C_{17}H_{15}N_3O_2$ mass spectrum: m/z=293 ($M^+$)

(10) 3-Z-(1-amino-1-methyl-methylene)-5-amido-2-indolinone

Prepared from the resin according to Example IV(2) and ammonia $R_f$ value: 0,23 (silica gel, methylene chloride/methanol= 9:1)

$C_{11}H_{11}N_3O_2$ mass spectrum: m/z=217 ($M^+$)

(11) 3-Z-[1-(4-piperidinomethyl-phenylamino)-1-methyl-methylene]-5-amido-2-indolinone
Prepared from the resin according to Example IV(2) and 4-(piperidinomethyl)-aniline
$R_f$ value: 0,31 (silica gel, methylene chloride/methanol= 9:1)
$C_{23}H_{26}N_4O_2$
mass spectrum: m/z=390 (M⁺)

(12) 3-Z-[1-(4-pyrrolidinomethyl-phenylamino)-1-methyl-methylene]-5-amido-2-indolinone
Prepared from the resin according to Example IV(2) and 4-pyrrolidinomethyl-aniline
$R_f$ value: 0.20 (silica gel, methylene chloride/methanol= 4:1)
$C_{22}H_{24}N_4O_2$
mass spectrum: m/z=376 (M⁺)

(13) 3-Z-[1-(4-Dipropylaminomethyl-phenylamino)-1-methyl-methylene]-5-amido-2-indolinone
Prepared from the resin according to Example 11(2) and 4-dipropylaminomethyl-aniline
$R_f$ value: 0.71 (silica gel, methylene chloride/methanol= 4:1)
$C_{24}H_{30}N_4O_2$
mass spectrum: m/z=406 (M⁺)

(14) 3-Z-[1-[4-(2-piperidinoethyl)-phenylamino]-1-methyl-methylene]-5-amido-2-indolinone
Prepared from the resin according to Example IV(2) and 4-(2-piperidinoethyl)-aniline
$R_f$ value: 0.38 (silica gel, methylene chloride/methanol= 4:1)
$C_{24}H_{28}N_4O_2$
mass spectrum: m/z=404 (M⁺)

(15) 3-Z-[1-[4-(2-diethylaminoethyl)-phenylamino]-1-methyl-methylene]-5-amido-2-indolinone
Prepared from the resin according to Example IV(2) and 4-(2-diethylaminoethyl)-aniline
$R_f$ value: 0.33 (silica gel, methylene chloride/methanol= 4:1)
$C_{23}H_{28}N_4O_2$
mass spectrum: m/z=393 (M⁺)

(16) 3-Z-[1-(4-Hexamethyleneiminomethyl-phenylamino)-1-methyl-methylene)-5-amido-2-indolinone
Prepared from the resin according to Example IV(2) and 4-hexamethyleneiminomethylaniline
$R_f$ value: 0.34 (silica gel, methylene chloride/methanol= 4:1)
$C_{24}H_{28}N_4O_2$
mass spectrum: m/z=404 (M⁺)

(17) 3-Z-[1-[4-(N-methyl-N-methansulphonyl-amino)-phenylamino]-1-methyl-methylene]-5-amido-2-indolinone
Prepared from the resin according to Example IV(2) and 4-(N-methyl-N-methanesulphonyl-amino)-aniline
$R_f$ value: 0.36 (silica gel, methylene chloride/methanol= 9:1)
$C_{19}H_{20}N_4O_4S$
mass spectrum: m/z=400 (M⁺)

(18) 3-Z-[1-(4-methanesulphonylamino-phenylamino)-1-methyl-methylene]-5-amido-2-indolinone
Prepared from the resin according to Example IV(2) and 4-methanesulphonylamino-aniline
$R_f$ value: 0.31 (silica gel, methylene chloride/methanol= 9:1)
$C_{18}H_{18}N_4O_4S$
mass spectrum: m/z=386 (M⁺)

(19) 3-Z-[1-(4-Bromophenylamino)-1-ethyl-methylene]-5-amido-2-indolinone
Prepared from the resin according to Example IV(3) and 4-bromoaniline
$R_f$ value: 0.52 (silica gel, methylene chloride/methanol= 9:1)
$C_{18}H_{16}BrN_3O_2$
mass spectrum: m/z=385/387 (M⁺/M+2⁺)

(20) 3-Z-[1-(4-piperidinomethyl-phenylamino)-1-ethyl-methylene]-5-amido-2-indolinone
Prepared from the resin according to Example IV(3) and 4-piperidinomethyl-aniline
$R_f$ value: 0.42 (silica gel, methylene chloride/methanol= 4:1)
$C_{24}H_{28}N_4O_2$
mass spectrum: m/z=404 (M⁺)

(21) 3-Z-[1-(4-piperidinomethyl-phenylamino)-1-propyl-methylene]-5-amido-2-indolinone
Prepared from the resin according to Example IV(4) and 4-piperidinomethyl-aniline
$R_f$ value: 0.49 (silica gel, methylene chloride/methanol= 4:1)
$C_{25}H_{30}N_4O_2$
mass spectrum: m/z=418 (M⁺)

(22) 3-Z-[1-(4-Bromophenylamino)-1-propyl-methylene]-5amido-2-indolinone
Prepared from the resin according to Example IV(4) and 4-bromoaniline
$R_f$ value: 0,53 (silica gel, methylene chloride/methanol= 9:1)
$C_{19}H_{18}BrN_3O_2$
mass spectrum: m/z=399/401 (M⁺/M+2⁺)

(23) 3-Z-[(4-Bromophenylamino)-methylene]-5-amido-2-indolinone
Prepared from the resin prepared according to Example IV(1) and 4-bromoaniline
$C_{16}H_{12}BrN_3O_2$
mass spectrum: m/z=357/359 (M⁺/M+2⁺)

(24) 3-Z-[(4-piperidinomethyl-phenylamino)-methylene]-5-amido-2-indolinone
Prepared from the resin prepared according to Example IV(1) and 4-piperidinomethyl-aniline
$C_{22}H_{24}N_4O_2$
mass spectrum: m/z=376 (M⁺)

(25) 3-Z-[1-(4-Bromophenylamino)-1-butyl-methylene]-5-amido-2-indolinone
Prepared from the resin according to Example IV and 4-bromoaniline
$R_f$ value: 0,53 (silica gel, methylene chloride/methanol= 9:1)
$C_{20}H_{20}BrN_3O_2$
mass spectrum: m/z=413/415 (M⁺/M+2⁺)

(26) 3-Z-[1-(4-piperidinomethyl-phenylamino)-1-butyl-methylene]-5-amido-2-indolinone Prepared from the resin according to Example IV and 4-piperidinomethyl-aniline $R_f$ value: 0.48 (silica gel, methylene chloride/methanol=4:1)

$C_{26}H_{32}N_4O_2$ mass spectrum: m/z=432 (M⁺)

(27) 3-Z-[1-(4-piperidinomethyl-phenylamino)-1-ethenyl-methylene]-5-amido-2-indolinone Prepared from the resin according to Example IV(5) and 4-piperidinomethyl-aniline

(28) 3-Z-[1-(4-piperidinomethyl-phenylamino)-1-(3-bromopropyl)-methylene]-5-amido-2-indolinone Prepared from the resin according to Example IV(6) and 4-piperidinomethyl-aniline

(29) 3-Z-[1-(4-piperidinomethyl-phenylamino)-1-(2-phenylsulphonylethyl)-methylene]-5-amido-2-indolinone Prepared from the resin according to Example IV(7) and 4-piperidinomethyl-aniline

(30) 3-Z-[1-[4-(2,6-dimethylpiperidinomethyl)-phenylamino]-1-methyl-methylene]-5-amido-5-amido-2-indolinone Prepared from the resin according to Example IV(2) and 4-(2,6-dimethylpiperidinomethyl)-aniline

(31) 3-Z-[1-(4-Thiomorpholinomethyl-phenylamino)-1-methyl-methylene]-5-amido-2-indolinone Prepared from the resin according to Example IV(2) and 4-thiomorpholinomethyl-aniline $R_f$ value: 0.53 (silica gel, methylene chloride/methanol=9:1)

$C_{22}H_{24}N_4O_2S$ mass spectrum: m/z=408 (M⁺)

(32) 3-Z-[1-[(4-Thiomorpholino-S-oxido-methyl)-phenylamino]-1-methyl-methylene]-5-amido-2-indolinone Prepared from the resin according to Example IV(2) and 4-(thiomorpholino-S-oxido-methyl)-aniline $R_f$ value: 0.21 (silica gel, methylene chloride/methanol=9:1)

$C_{22}H_{24}N_4O_3S$ mass spectrum: m/z =424 (M⁺)

(33) 3-Z-[1-[4-(Thiomorpholino-S,S-dioxido-methyl)-phenylamino]-1-methyl-methylene]-5-amido-2-indolinone Prepared from the resin according to Example IV(2) and 4-(thiomorpholino-S,S-dioxido-methyl)-aniline

(34) 3-Z-[1-(4-Azetidionomethyl-phenylamino)-1-methyl-methylene]-5-amido-2-indolinone Prepared from the resin according to Example IV(2) and 4-azetidionomethyl-aniline

(35) 3-Z-[1-[4-(2,5-Dihydropyrrol-1-yl-methyl)-phenylamino]-1-methyl-methylene]-5-amido-2-indolinone Prepared from the resin according to Example IV(2) and 4-(2,5-dihydropyrrol-1-yl-methyl)-aniline $R_f$ value: 0.10 (silica gel, methylene chloride/methanol=9:1)

$C_{22}H_{22}N_4O_2$ mass spectrum: m/z=375 (M+H⁺)

(36) 3-Z-[1-[4-(3,6-Dihydro-2H-pyridin-1-yl-methyl)-phenylamino]-1-methyl-methylene]-5-amido-2-indolinone Prepared from the resin according to Example IV(2) and 4-(3,6-dihydro-2H-pyridin-1-yl-methyl)-aniline $R_f$ value: 0.20 (silica gel, methylene chloride/methanol=9:1)

$C_{23}H_{24}N_4O_2$ mass spectrum: m/z=389 (M+H)⁺

(37) 3-Z-[1-[4-(2-ethoxycarbonyl-pyrrolidinomethyl)-phenylamino]-1-methyl-methylene]-5-amido-2-indolinone Prepared from the resin according to Example IV(2) and 4-(2-ethoxycarbonyl-pyrrolidinomethyl)-aniline $R_f$ value: 0.50 (silica gel, methylene chloride/methanol=9:1)

$C_{24}H_{26}N_4O_4$ mass spectrum: m/z=435 (M+H)⁺

(38) 3-Z-[1-[4-(3,5-dimethyl-piperidinomethyl)-phenylamino]-1-methyl-methylene]-5-amido-2-indolinone Prepared from the resin according to Example IV(2) and 4-(3,5-dimethyl-piperidinomethyl)-aniline $R_f$ value: 0.16 (silica gel, methylene chloride/methanol=9:1)

$C_{25}H_{30}N_4O_2$ mass spectrum: m/z=418 (M⁺)

(39) 3-Z-[1-[4-(4-phenyl-piperazinylmethyl)-phenylamino]-1-methyl-methylene]-5-amido-2-indolinone-trifluoroacetate Prepared from the resin according to Example IV(2) and 4-(4-phenyl-piperazinylmethyl)-aniline $R_f$ value: 0.40 (silica gel, methylene chloride/methanol=9:1)

$C_{28}H_{29}N_5O_2$ mass spectrum: m/z=468 (M+H)⁺

(40) 3-Z-[1-[4-(4-phenyl-4-hydroxy-piperidinylmethyl)-phenylamino]-1-methyl-methylene]-5-amido-2-indolinone-trifluoroacetate Prepared from the resin according to Example IV(2) and 4-(4-phenyl-4-hydroxy-piperidinylmethyl)-aniline $C_{29}H_{30}N_4O_3$ mass spectrum: m/z=483 (M+H)⁺

(41) 3-Z-[1-(3-methoxy-phenylamino)-1-methyl-methylene]-5-amido-2-indolinone

Prepared from the resin according to Example IV(2) and 3-methoxy-aniline $R_f$ value: 0.40 (silica gel, methylene chloride/methanol=9:1)

$C_{18}H_{17}N_3O_3$

Mass spectrum: m/z=323 (M⁺)

(42) 3-Z-[1-(3-ethoxycarbonyl-phenylamino)-1-methyl-methylene]-5-amido-2-indolinone Prepared from the resin according to Example IV(2) and ethyl 3-amino-benzoate $C_{20}H_{19}N_3O_4$ Mass spectrum: m/z=365 (M⁺)

(43) 3-Z-[1-(4-dimethylaminomethyl-phenylamino)-1-methylmethylen]-5-amido-2-indolinone trifluoroacetate Prepared from the resin according to Example IV(2) and 4-dimethylaminomethyl-aniline $C_{20}H_{22}N_4O_2$ Mass spectrum: m/z=351 (M+H⁺)

(44) 3-Z-[1-[4-(4-Cyclohexyl-piperidinylmethyl)-phenylamino]-1-methyl-methylene]-5-amido-2-indolinone
Prepared from the resin according to Example IV(2) and 4-(4-cyclohexyl-piperidinylmethyl)-aniline

(45) 3-Z-[1-(4-morpholinyl-phenylamino)-1-methyl-methylene]-5-amido-2-indolinone
Prepared from the resin according to Example IV(2) and 4-morpholinyl-aniline
$C_{21}H_{22}N_4O_3$
Mass spectrum: m/z=378 (M⁺)

(46) 3-Z-[1-(N-methyl-piperidin-4-ylamino)-1-methyl-methylene)-5-amido-2-indolinone
Prepared from the resin according to Example IV(2) and 4-amino-N-methyl-piperidine
$C_{17}H_{22}N_4O_2$
Mass spectrum: m/z=314 (M⁺)

(47) 3-Z-[1-(4-methylcyclohexylamino)-1-methyl-methylene]-5-amido-2-indolinone
Prepared from the resin according to Example IV(2) and 4-methyl-cyclohexylamine
$C_{18}H_{23}N_3O_2$
Mass spectrum: m/z=313 (M⁺)

(48) 3-Z-(1-Cyclopentylamino-1-methyl-methylene)-5-amido-2-indolinone
Prepared from the resin according to Example IV(2) and cyclopentylamine
$R_f$ value: 0.70 (silica gel, methylene chloride/methanol=4:1)
$C_{16}H_{19}N_3O_2$
Mass spectrum: m/z=285 (M⁺)

(49) 3-Z-(1-isopropylamino-1-methyl-methylene)-5-amido-2-indolinone
Prepared from the resin according to Example IV(2) and isopropylamine
$C_{14}H_{17}N_3O_2$
Mass spectrum: m/z=259 (M⁺)

(50) 3-Z-[1-(4-ethoxycarbonylmethylaminomethyl-phenylamino)-1-methyl-methylene]-5-amido-2-indolinone
Prepared from the resin according to Example IV(2) and 4-(ethoxycarbonylmethyl -N-tert.butyloxycarbonyl-aminomethyl)-aniline
$C_{21}H_{22}N_4O_4$
Mass spectrum: m/z=394 (M⁺)

(51) 3-Z-[1-(4-benzylaminomethyl-phenylamino)-1-methyl-methylene]-5-amido-2-indolinone
Prepared from the resin according to Example IV(2) and 4-(N-benzyl-N-tert.butyloxycarbonyl-aminomethyl)-aniline
$R_f$ value: 0.24 (silica gel, methylene chloride/methanol=9:1)
$C_{25}H_{24}N_4O_2$
Mass spectrum: m/z=412 (M⁺)

(52) 3-Z-[1-(4-Butylaminomethyl-phenylamino)-1-methyl-methylene]-5-amido-2-indolinone trifluoroacetate
Prepared from the resin according to Example IV(2) and 4-(N-butyl-N-tert.butyloxycarbonyl-aminomethyl)-aniline
$R_f$ value: 0.40 (silica gel, methylene chloride/methanol=4:1)
$C_{22}H_{26}N_4O_2$
Mass spectrum: m/z=378 (M⁺)

(53) 3-Z-[1-(4-ethylaminomethyl-phenylamino)-1-methyl-methylene]-5-amido-2-indolinone trifluoroacetate
Prepared from the resin according to Example IV(2) and 4-(N-ethyl-N-tert.butyloxycarbonyl-aminomethyl)-aniline
$R_f$ value: 0.20 (silica gel, methylene chloride/methanol=4:1)
$C_{20}H_{22}N_4O_2$
Mass spectrum: m/z=351 (M+H⁺)

(54) 3-Z-[1-(4-Cyclohexylaminomethyl-phenylamino)-1-methyl-methylene]-5-amido-2-indolinone trifluoroacetate
Prepared from the resin according to Example IV(2) and 4-(cyclohexyl-(N-tert.butyloxycarbonyl-amino-methyl)-aniline
$C_{24}H_{28}N_4O_2$
Mass spectrum: m/z=405 (M⁺)

(55) 3-Z-[1-(4-isopropylaminomethyl-phenylamino)-1-methyl-methylene]-5-amido-2-indolinone trifluoroacetate
Prepared from the resin according to Example IV(2) and 4-(N-isopropyl-N-tert.butyloxycarbonyl-aminomethyl)-aniline
$C_{21}H_{24}N_4O_2$
Mass spectrum: m/z=365 (M⁺)

(56) 3-Z-[1-(4-trifluoromethoxy-phenylamino)-1-methyl-methylene]-5-amido-2-indolinone
Prepared from the resin produced in Example IV(2) and 4-trifluoromethoxy-aniline
$C_{18}H_{14}F_3N_3O_3$
mass spectrum: m/z=377 (M⁺)

(57) 3-Z-[1-(4-difluoromethoxy-phenylamino)-1-methyl-methylene]-5-amido-2-indolinone
Prepared from the resin produced in Example IV(2) and 4-difluoromethoxy-aniline
$R_f$ value: 0.5 (silica gel, methylene chloride/methanol=9:1)
$C_{18}H_{15}F_2N_3O_3$
mass spectrum: m/z=359 (M+H⁺)

(58) 3-Z-[1-(4-bromo-3-chloro-phenylamino)-1-methyl-methylene]-5-amido-2-indolinone
Prepared from the resin produced in Example IV(2) and 4-bromo-3-chloro-aniline
$C_{17}H_{13}BrClN_3O_2$
mass spectrum: m/z=405/407/409 (M⁺/M+2⁺/M+4⁺)

(59) 3-Z-[1-(4-trifluoromethyl-3-bromo-phenylamino)-1-methyl-methylene]-5-amido-2-indolinone
Prepared from the resin produced in Example IV(2) and 4-trifluoromethyl-3-bromo-aniline
$C_{18}H_{13}BrF_3N_3O_2$
mass spectrum: m/z=439/441 (M⁺/M+2⁺)

(60) 3-Z-[1-(4-chloro-phenylamino)-methylene]-5-amido-2-indolinone
Prepared from the resin produced in Example IV(1) and 4-chloro-aniline
$C_{16}H_{12}ClN_3O_2$
mass spectrum: m/z=312/314 (M⁺)

(61) 3-Z-[1-(3-bromo-phenylamino)-1-methyl-methylene]-5-amido-2-indolinone

Prepared from the resin produced in Example IV(2) and 3-bromo-aniline $C_{17}H_{14}BrN_3O_2$ mass spectrum: m/z=371/373 (M⁺)

(62) 3-Z-[1-(3-chloro-phenylamino)-1-methyl-methylene]-5-amido-2-indolinone

Prepared from the resin produced in Example IV(2) and 3-chloro-aniline $C_{17}H_{14}ClN_3O_2$ mass spectrum: m/z=327/329 (M⁺)

(63) 3-Z-[1-(2-chloro-phenylamino)-1-methyl-methylene]-5-amido-2-indolinone

Prepared from the resin produced in Example IV(2) and 2-chloro-aniline $C_{17}H_{14}ClN_3O_2$ mass spectrum: m/z=327/329 (M⁺)

(64) 3-Z-[1-(4-bromo-3-methyl-phenylamino)-1-methyl-methylene]-5-amido-2-indolinone Prepared from the resin produced in Example IV(2) and 4-bromo-3-methyl-aniline $R_f$ value: 0.60 (silica gel, methylene chloride/methanol= 9:1)

$C_{18}H_{16}BrN_3O_2$ mass spectrum: m/z=385/387 (M⁺)

(65) 3-Z-[1-(4-bromo-3-methoxy-phenylamino)-1-methyl-methylene]-5-amido-2-indolinone Prepared from the resin produced in Example IV(2) and 4-bromo-3-methoxy-aniline $R_f$ value: 0.60 (silica gel, methylene chloride/methanol= 9:1)

$C_{18}H_{16}BrN_3O_3$ mass spectrum: m/z=401/403 (M⁺)

(66) 3-Z-[1-(4-fluoro-3-nitro-phenylamino)-1-methyl-methylene]-5-amido-2-indolinone Prepared from the resin produced in Example IV(2) and 4-fluoro-3-nitro-aniline $R_f$ value: 0.40 (silica gel, methylene chloride/methanol= 9:1)

$C_{17}H_{13}FN_4O_4$ mass spectrum: m/z=356 (M⁺)

(67) 3-Z-[1-(4-bromo-3-nitro-phenylamino)-1-methyl-methylene]-5-amido-2-indolinone Prepared from the resin produced in Example IV(2) and 4-bromo-3-nitro-aniline $R_f$ value: 0.50 (silica gel, methylene chloride/methanol= 9:1)

$C_{17}H_{13}BrN_4O_4$ mass spectrum: m/z=416/418 (M⁺)

(68) 3-Z-[1-(4-Ethyl-3-nitro-phenylamino)-1-methyl-methylene]-5-amido-2-indolinone Prepared from the resin produced in Example IV(2) and 4-ethyl-3-nitro-aniline $R_f$ value: 0.70 (silica gel, methylene chloride/methanol= 9:1)

$C_{19}H_{18}N_4O_4$ mass spectrum: m/z=366 (M⁺)

(69) 3-Z-[1-(4-chloro-3-nitro-phenylamino)-1-methyl-methylene]-5-amido-2-indolinone Prepared from the resin produced in Example IV(2) and 4-chloro-3-nitro-aniline $C_{17}H_{13}ClN_4O_4$ mass spectrum: m/z=371/373 (M⁺)

(70) 3-Z-[1-(3-Nitro-phenylamino)-1-methyl-methylene]-5-amido-2-indolinone

Prepared from the resin produced in Example IV(2) and 3-nitro-aniline $C_{17}H_{14}N_4O_4$ mass spectrum: m/z=338 (M+H⁺)

(71) 3-Z-[1-(4-Methyl-3-nitro-phenylamino)-1-methyl-methylene]-5-amido-2-indolinone Prepared from the resin produced in Example IV(2) and 4-methyl-3-nitro-aniline $R_f$ value: 0.50 (silica gel, methylene chloride/methanol= 9:1)

$C_{18}H_{16}N_4O_4$ mass spectrum: m/z=352 (M⁺)

(72) 3-Z-[1-(4-bromo-3-methoxycarbonyl-phenylamino)-1-methyl-methylene]-5-amido-2-indolinone Prepared from the resin produced in Example IV(2) and methyl 2-bromo-5-aminobenzoate $R_f$ value: 0.50 (silica gel, methylene chloride/methanol= 9:1)

$C_{19}H_{16}BrN_3O_4$ mass spectrum: m/z=429/431 (M+H⁺)

(73) 3-Z-[1-(4-Carbamoyl-phenylamino)-1-methyl-methylene]-5-amido-2-indolinone

Prepared from the resin produced in Example IV(2) and 4-aminobenzamide $R_f$ value: 0,20 (silica gel, methylene chloride/methanol= 9:1)

$C_{18}H_{16}N_4O_3$ mass spectrum: m/z=336 (M⁺)

(74) 3-Z-[1-(4-(Piperidino-carbonyl)-phenylamino)-1-methyl-methylene]-5-amido-2-indolinone Prepared from the resin produced in Example IV(2) and 1-(4-amino-benzoyl)-piperidine $R_f$ value: 0.50 (silica gel, methylene chloride/methanol= 9:1)

$C_{23}H_{24}N_4O_3$ mass spectrum: m/z=404 (M⁺)

(75) 3-Z-[1-(4-(2-(diethylamino)-ethyl-carbamoyl)-phenylamino)-1-methyl-methylene]-5-amido-2-indolinone-trifluoracetate Prepared from the resin produced in Example IV(2) and 4-amino-N-[2-(diethylamino)-ethyl]-benzamide $R_f$ value: 0.30 (silica gel, methylene chloride/methanol= 9:1)

$C_{24}H_{29}N_5O_3$ mass spectrum: m/z=436 (M+H⁺)

(76) 3-Z-[1-(4-trifluoromethyl-phenylamino)-1-methyl-methylene]-5-amido-2-indolinone Prepared from the resin produced in Example IV(2) and 4-trifluoromethyl-aniline $C_{18}H_{14}F_3N_3O_2$ mass spectrum: m/z=361 (M⁺)

(77) 3-Z-[1-(3-Hydroxymethyl-phenylamino)-1-methyl-methylene]-5-amido-2-indolinone Prepared from the resin produced in Example IV(2) and 3-aminobenzylalcohol

(78) 3-Z-[1-(4-(Hydroxycarbonyl-phenylamino)-1-methyl-methylene]-5-amido-2-indolinone
Prepared from the resin produced in Example IV(2) and 4-aminobenzoic acid
$R_f$ value: 0.20 (silica gel, methylene chloride/methanol= 4:1)
$C_{18}H_{15}N_3O_4$
mass spectrum: m/z=336 (M–H$^+$)

(79) 3-Z-[1-(4-Ethoxycarbonylmethyl-3-nitro-phenylamino)-1-methyl-methylene]-5-amido-2-indolinone
Prepared from the resin produced in Example IV(2) and ethyl 4-amino-2-nitro-phenylacetate
$R_f$ value: 0.70 (silica gel, methylene chloride/methanol= 9:1)
$C_{21}H_{20}N_4O_6$
mass spectrum: m/z=424 (M$^+$)

(80) 3-Z-[1-(3-Methoxycarbonyl-4-methyl-phenylamino)-1-methyl-methylene]-5-amido-2-indolinone
Prepared from the resin produced in Example IV(2) and methyl 3-amino-6-methyl-benzoate
$R_f$ value: 0.70 (silica gel, methylene chloride/methanol= 9:1)
$C_{20}H_{19}N_3O_4$
mass spectrum: m/z=365 (M$^+$)

(81) 3-Z-[1-(3-Diethylcarbamoyl-4-methyl-phenylamino)-1-methyl-methylene]-5-amido-2-indolinone
Prepared from the resin produced in Example IV(2) and 3-amino-6-methyl-benzoic acid diethylamide
$R_f$ value: 0.50 (silica gel, methylene chloride/methanol= 9:1)
$C_{23}H_{26}N_4O_3$
mass spectrum: m/z=406 (M$^+$)

(82) 3-Z-[1-(3-Ethylcarbamoyl-4-methyl-phenylamino)-1-methyl-methylene]-5-amido-2-indolinone
Prepared from the resin produced in Example IV(2) and 3-amino-6-methyl-benzoic acid ethylamide
$R_f$ value: 0.40 (silica gel, methylene chloride/methanol= 9:1)
$C_{21}H_{22}N_4O_3$
mass spectrum: m/z=378 (M$^+$)

(83) 3-Z-[1-(3-Sulphamoyl-4-methyl-phenylamino)-1-methyl-methylene]-5-amido-2-indolinone
Prepared from the resin produced in Example IV(2) and 3-amino-6-methyl-phenylsulphonic acid amide
$R_f$ value: 0.30 (silica gel, methylene chloride/methanol= 9:1)
$C_{18}H_{18}N_4O_4S$
mass spectrum: m/z=386 (M$^+$)

(84) 3-Z-[1-(3-Acetylamino-4-methyl-phenylamino)-1-methyl-methylene]-5-amido-2-indolinone
Prepared from the resin produced in Example IV(2) and 4-amino-2-acetylamino-toluene
$R_f$ value: 0.65 (silica gel, methylene chloride/methanol= 9:1)
$C_{20}H_{20}N_4O_3$
mass spectrum: m/z=364 (M$^+$)

(85) 3-Z-[1-(4-(2-Dimethylamino-ethoxy)-phenylamino)-1-methyl-methylene]-5-amido-2-indolinone-trifluoroacetate
Prepared from the resin produced in Example IV(2) and 4-(2-dimethylamino-ethoxy)-aniline
$R_f$ value: 0,10 (silica gel, methylene chloride/methanol= 4:1)
$C_{21}H_{24}N_4O_3$
mass spectrum: m/z=380 (M$^+$)

(86) 3-Z-[1-(4-(2-Piperidino-ethoxy)-phenylamino)-1-methyl-methylene]-5-amido-2-indolinone-trifluoroacetate
Prepared from the resin produced in Example IV(2) and 4-(2-piperidino-ethoxy)-aniline
$R_f$ value: 0.70 (silica gel, methylene chloride/methanol= 4:1)
$C_{24}H_{28}N_4O_3$
mass spectrum: m/z=420 (M$^+$)

(87) 3-Z-[1-(4-(3-Dimethylamino-propoxy)-phenylamino)-1-methyl-methylene]-5-amido-2-indolinone-trifluoroacetate
Prepared from the resin produced in Example IV(2) and 4-(3-dimethylamino-propoxy)-aniline
$R_f$ value: 0.10 (silica gel, methylene chloride/methanol= 4:1)
$C_{22}H_{26}N_4O_3$
mass spectrum: m/z=394 (M$^+$)

(88) 3-Z-[1-(4-(3-Piperidino-propoxy)-phenylamino)-1-methyl-methylene]-5-amido-2-indolinone-trifluoroacetate
Prepared from the resin produced in Example IV(2) and 4-(3-piperidino-propoxy)-aniline
$R_f$ value: 0.20 (silica gel, methylene chloride/methanol= 4:1)
$C_{25}H_{30}N_4O_3$
mass spectrum: m/z=434 (M$^+$)

(89) 3-Z-[1-(4-(3-(N-Benzyl-N-methylamino)-propoxy)-phenylamino)-1-methyl-methylene]-5-amido-2-indolinone-trifluoroacetate
Prepared from the resin produced in Example IV(2) and 4-[3-(N-benzyl-N-methylamino)-propoxy]-aniline
$R_f$ value: 0.60 (silica gel, methylene chloride/methanol= 4:1)
$C_{28}H_{30}N_4O_3$
mass spectrum: m/z=470 (M$^+$)

(90) 3-Z-[1-(4-(N-benzyl-aminomethyl)-phenylamino)-methylene]-5-amido-2-indolinone-trifluoroacetate
Prepared from the resin produced in Example IV(1) and 4-(N-benzyl-N-tert.butoxcarbonyl-aminomethyl)-aniline
$C_{24}H_{22}N_4O_2$
mass spectrum: m/z=399 (M+H$^+$)

(91) 3-Z-[1-(4-(N-(4-chlorobenzyl)-aminomethyl)-phenylamino)-1-methyl-methylene]-5-amido-2-indolinone-trifluoroacetate
Prepared from the resin produced in Example IV(2) and 4-[N-(4-chlorobenzyl-N-tert.butoxycarbonyl-aminomethyl)-aniline
$R_f$ value: 0.40 (silica gel, methylene chloride/methanol= 9:1)
$C_{25}H_{23}ClN_4O_2$
mass spectrum: m/z=446/448 (M$^+$)

(92) 3-Z-[1-(4-(N-(3,4,5-Trimethoxybenzyl)-N-methyl-aminomethyl)-phenylamino)-1-methyl-methylene]-5-amido-2-indolinone-trifluoroacetate Prepared from the resin produced in Example IV(2) and 4-[N-((3,4,5-trimethoxy-benzyl)-N-methyl-aminomethyl]-aniline $R_f$ value: 0.50 (silica gel, methylene chloride/methanol= 9:1)

$C_{29}H_{32}N_4O_5$ mass spectrum: m/z=516 (M$^+$)

(93) 3-Z-[1-(4-(N-(3,4-Dimethoxy-benzyl)-N-methyl-amino-methyl)-phenylamino)-1-methyl-methylene]-5-amido-2-indolinone-trifluoroacetate Prepared from the resin produced in Example IV(2) and 4-[N-(3,4-dimethoxy-benzyl)-N-methyl-aminomethyl]-aniline $R_f$ value: 0.40 (silica gel, methylene chloride/methanol= 9:1)

$C_{28}H_{30}N_4O_4$ mass spectrum: m/z=486 (M$^+$)

(94) 3-Z-[1-(4-(N-(3,4-Dimethoxy-benzyl)-N-ethyl-aminomethyl)-phenylamino)-1-methyl-methylene]-5-amido-2-indolinone-trifluoroacetate Prepared from the resin produced in Example IV(2) and 4-[N-(3,4-dimethoxy-benzyl)-N-ethyl-aminomethyl]-aniline $R_f$ value: 0.40 (silica gel, methylene chloride/methanol= 9:1)

$C_{29}H_{32}N_4O_4$ mass spectrum: m/z=500 (M$^+$)

(95) 3-Z-[1-(4-(N-Benzyl-N-ethyl-aminomethyl)-phenylamino)-1-methyl-methylene]-5-amido-2-indolinone-trifluoroacetate Prepared from the resin produced in Example IV(2) and 4-(N-benzyl-N-ethyl-aminomethyl)-aniline $R_f$ value: 0.50 (silica gel, methylene chloride/methanol= 9:1)

$C_{27}H_{28}N_4O_2$ mass spectrum: m/z=440 (M$^+$)

(96) 3-Z-[1-(4-(N-Benzyl-N-methyl-aminomethyl)-phenylamino)-1-methyl-methylene]-5-amido-2-indolinone-trifluoroacetate Prepared from the resin produced in Example IV(2) and 4-(N-benzyl-N-methyl-aminomethyl)-aniline $R_f$ value: 0,55 (silica gel, methylene chloride/methanol= 9:1)

$C_{26}H_{26}N_4O_2$ mass spectrum: m/z=426 (M$^+$)

(97) 3-Z-[1-(4-(N-Benzyl-N-methyl-aminomethyl)-phenylamino)-1-ethyl-methylene]-5-amido-2-indolinone-trifluoroacetate Prepared from the resin produced according to Example IV(3) and 4-(N-benzyl-N-methyl-aminomethyl)-aniline $R_f$ value: 0.50 (silica gel, methylene chloride/methanol= 9:1)

$C_{27}H_{28}N_4O_2$ mass spectrum: m/z=440 (M$^+$)

(98) 3-Z-[1-(4-(N-Benzyl-N-methyl-aminomethyl)-phenylamino)-1-propyl-methylene]-5-amido-2-indolinone-trifluoroacetate Prepared from the resin produced according to Example IV(4) and 4-(N-benzyl-N-methyl-amino-methyl)-aniline $R_f$ value: 0.50 (silica gel, methylene chloride/methanol= 9:1)

$C_{28}H_{30}N_4O_2$ mass spectrum: m/z=454 (M$^+$)

(99) 3-Z-[1-(4-(N-(4-chlorobenzyl)-N-methyl-aminomethyl)-phenylamino)-1-methyl-methylene]-5-amido-2-indolinone-trifluoroacetate Prepared from the resin produced in Example IV(2) and 4-[N-(4-chlorobenzyl)-N-methyl-aminomethyl]-aniline $R_f$ value: 0.40 (silica gel, methylene chloride/methanol= 9:1)

$C_{26}H_{25}ClN_4O_2$ mass spectrum: m/z=460/462 (M$^+$)

(100) 3-Z-[1-(4-(N-(3-chlorobenzyl)-N-methyl-aminomethyl)-phenylamino)-1-methyl-methylene]-5-amido-2-indolinone-trifluoroacetate Prepared from the resin produced in Example IV(2) and 4-[N-(3-chlorobenzyl)-N-methyl-aminomethyl]-aniline $R_f$ value: 0.40 (silica gel, methylene chloride/methanol= 9:1)

$C_{26}H_{25}ClN_4O_2$ mass spectrum: m/z=460/462 (M$^+$)

(101) 3-Z-[1-(4-(N-(2,6-dichlorobenzyl)-N-methyl-aminomethyl)-phenylamino)-1-methyl-methylene]-5-amido-2-indolinone-trifluoroacetate Prepared from the resin produced in Example IV(2) and 4-[N-(2,6-dichlorobenzyl)-N-methyl-aminomethyl]-aniline $R_f$ value: 0,38 (silica gel, methylene chloride/methanol= 9:1)

$C_{26}H_{24}Cl_2N_4O_2$ mass spectrum: m/z=494/496/498 (M+2$^+$/M+4$^+$)

(102) 3-Z-[1-(4-(N-(4-trifluoromethylbenzyl)-N-methyl-aminomethyl)-phenylamino)-1-methyl-methylene]-5-amido-2-indolinone-trifluoroacetate Prepared from the resin produced in Example IV(2) and 4-[N-(4-trifluoromethylbenzyl)-N-methyl-aminomethyl]-aniline $R_f$ value: 0,38 (silica gel, methylene chloride/methanol= 9:1)

$C_{27}H_{25}F_3N_4O_2$ mass spectrum: m/z=494 (M$^+$)

(103) 3-Z-[1-(4-(N-Benzyl-N-isopropyl-aminomethyl)-phenylamino)-1-methyl-methylene]-5-amido-2-indolinone-trifluoroacetate Prepared from the resin produced in Example IV(2) and 4-(N-benzyl-N-isopropyl-aminomethyl)-aniline $R_f$ value: 0.50 (silica gel, methylene chloride/methanol= 9:1)

$C_{28}H_{30}N_4O_2$ mass spectrum: m/z=454 (M$^+$)

(104) 3-Z-[1-(4-(N-benzyl-N-tert.butyl-aminomethyl)-phenylamino)-1-methyl-methylene]-5-amido-2-indolinone-trifluoroacetate Prepared from the resin produced in Example IV(2) and 4-(N-benzyl-N-tert.butyl-aminomethyl)-aniline $R_f$ value: 0.50 (silica gel, methylene chloride/methanol= 9:1)

$C_{29}H_{32}N_4O_2$ mass spectrum: m/z=468 (M$^+$)

(105) 3-Z-[1-(4-(N-benzyl-N-methyl-aminomethyl)-phenylamino)-methylene]-5-amido-2-indolinone-trifluoroacetate Prepared from the resin produced in Example IV(1) and 4-(N-benzyl-N-methyl-aminomethyl)-aniline $C_{25}H_{24}N_4O_2$ mass spectrum: m/z=413 (M+H⁺)

(106) 3-Z-[1-(4-(N-benzyl-N-ethyl-aminomethyl)-phenylamino)-1-methyl-methylene]-5-amido-2-indolinone-trifluoroacetate Prepared from the resin produced in Example IV(I) and 4-(N-benzyl-N-ethyl-aminomethyl)-aniline $C_{26}H_{26}N_4O_2$ mass spectrum: m/z=427 (M+H⁺)

(107) 3-Z-[1-(4-(Diisopropylamino-methyl)-phenylamino)-1-methyl-methylene]-5-amido-2-indolinone-trifluoroacetate Prepared from the resin produced in Example IV(2) and 4-(diisopropylamino-methyl)-aniline $R_f$ value: 0.50 (silica gel, methylene chloride/methanol=4:1)

$C_{24}H_{30}N_4O_2$ mass spectrum: m/z=406 (M⁺)

(108) 3-Z-[1-(4-(Di-n-propylamino-methyl)-phenylamino)-methylene]-5-amido-2-indolinone-trifluoroacetate Prepared from the resin produced in Example IV(2) and 4-(di-n-propylamino-methyl)-aniline $C_{23}H_{28}N_4O_2$ mass spectrum: m/z=393 (M+H⁺)

(109) 3-Z-[1-(4-(diisobutylamino-methyl)-phenylamino)-1-methyl-methylene]-5-amido-2-indolinone-trifluoroacetate Prepared from the resin produced in Example IV(2) and 4-(diisobutylamino-methyl)-aniline $R_f$ value: 0.50 (silica gel, methylene chloride/methanol=9:1)

$C_{26}H_{34}N_4O_2$ mass spectrum: m/z=434 (M⁺)

(110) 3-Z-[1-(4-(2,3,4,5-Tetrahydro-benzo(d)azepin-3-yl-methyl)-phenylamino)-1-methyl-methylene]-5-amido-2-indolinone-trifluoroacetate Prepared from the resin produced in Example IV(2) and 4-(2,3,4,5-tetrahydro-benzo(d)azepin-3-yl-methyl)-aniline $R_f$ value: 0.30 (silica gel, methylene chloride/methanol=9:1)

$C_{28}H_{28}N_4O_2$ mass spectrum: m/z=452 (M⁺)

(111) 3-Z-[1-(4-(1,3-Dihydro-isoindol-2-yl-methyl)-phenylamino)-1-methyl-methylene]-5-amido-2-indolinone-trifluoroacetate Prepared from the resin produced in Example IV(2) and 4-(1,3-dihydro-isoindol-2-yl-methyl)-aniline $R_f$ value: 0,35 (silica gel, methylene chloride/methanol=9:1)

$C_{26}H_{24}N_4O_2$ mass spectrum: m/z=425 (M+H⁺)

(112) 3-Z-[1-(4-(6,7-Dimethoxy-1,2,3,4-tetrahydro-isoquinolin-2-yl-methyl)-phenylamino)-1-methyl-methylene]-5-amido-2-indolinone-trifluoroacetate Prepared from the resin produced in Example IV(2) and 4-(6,7-dimethoxy-1,2,3,4-tetrahydro-isoquinolin-2-yl-methyl)-aniline $R_f$ value: 0.50 (silica gel, methylene chloride/methanol=9:1)

$C_{29}H_{30}N_4O_4$ mass spectrum: m/z=499 (M+H⁺)

(113) 3-Z-[1-(4-(1,2,3,4-tetrahydro-isoquinolin-2-yl-methyl)-phenylamino)-1-methyl-methylene]-5-amido-2-indolinone-trifluoroacetate Prepared from the resin produced in Example IV(2) and 4-(1,2,3,4-tetrahydro-isoquinolin-2-yl-methyl)-aniline (114) 3-Z-[1-(4-(N-(Ethoxycarbonylmethyl)-N-benzyl-aminomethyl)-phenylamino)-1-methyl-methylene]-5-amido-2-indolinone-trifluoroacetate Prepared from the resin produced in Example IV(2) and 4-[N-(ethoxycarbonylmethyl)-N-benzyl-aminomethyl)-aniline $R_f$ value: 0.60 (silica gel, methylene chloride/methanol=9:1)

$C_{29}H_{30}N_4O_4$ mass spectrum: m/z=498 (M⁺)

(115) 3-Z-[1-(4-(N-(2-Hydroxyethyl)-N-benzyl-aminomethyl)-phenylamino)-1-methyl-methylene]-5-amido-2-indolinone-trifluoracetate Prepared from the resin produced in Example IV(2) and 4-[N-(2-hydroxyethyl)-N-benzyl-aminomethyl)-aniline $R_f$ value: 0.40 (silica gel, methylene chloride/methanol=9:1)

$C_{27}H_{28}N_4O_3$ mass spectrum: m/z=456 (M⁺)

(116) 3-Z-[1-(4-(N-(1-Ethyl-pentyl)-N-(pyridin-2-yl-methyl)-aminomethyl)-phenylamino)-1-methyl-methylene]-5-amido-2-indolinone-trifluoroacetate Prepared from the resin produced in Example IV(2) and 4-[N-(1-ethyl-pentyl)-N-(pyridin-2-yl-methyl)-aminomethyl]-aniline $R_f$ value: 0,45 (silica gel, methylene chloride/methanol=9:1)

$C_{31}H_{37}N_5O_2$ mass spectrum: m/z=511 (M⁺)

(117) 3-Z-[1-(4-(Piperidino-methyl)-3-nitro-phenylamino)-1-methyl-methylene]-5-amido-2-indolinone Prepared from the resin produced in Example IV(2) and 4-(piperidino-methyl)-3-nitro-aniline $R_f$ value: 0.70 (silica gel, methylene chloride/methanol=9:1)

$C_{23}H_{25}N_5O_4$ mass spectrum: m/z=436 (M+H⁺)

(118) 3-Z-[1-(4-(N-Phenethyl-N-methyl-aminomethyl)-phenylamino)-1-methyl-methylene]-5-amido-2-indolinone-trifluoroacetate Prepared from the resin produced in Example IV(2) and 4-(N-phenethyl-N-methyl-aminomethyl)-aniline $R_f$ value: 0.50 (silica gel, methylene chloride/methanol=9:1)

$C_{27}H_{28}N_4O_2$ mass spectrum: m/z=441 (M+H⁺)

(119) 3-Z-[1-(4-(N-phenethyl-N-ethyl-aminomethyl)-phenylamino)-1-methyl-methylene]-5-amido-2-indolinone (120) 3-Z-[1-(4-(N-(3,4-dihydroxy-phenethyl)-N-methyl-amino-methyl)-phenylamino)-1-methyl-methylene]-5-amido-2-indolinone (121) 3-Z-[1-(4-(N-(3,4,5-trimethoxy-phenethyl)-N-methyl-aminomethyl)-phenylamino)-1-methyl-methylene]-5-amido-2-indolinone (122) 3-Z-[1-(4-(N-(3,4-dimethoxy-phenethyl)-N-methyl-amino-methyl)-phenylamino)-1-methyl-methylene]-5-amido-2-indolinone (123) 3-Z-[1-(4-(N-(4-nitro-phenethyl)-N-methyl-aminomethyl)-phenylamino)-1-methyl-methylene]-5-amido-2-indolinone (124) 3-Z-[1-(4-(N-phenethyl-N-benzyl-aminomethyl)-phenylamino)-1-methyl-methylene]-5-amido-2-indolinone $C_{33}H_{32}N_4O_2$ mass spectrum: m/z=517 (M+H$^+$)

$R_f$ value: 0,43 (silica gel, methylene chloride/methanol=9:1)

(125) 3-Z-[1-(4-(N-phenethyl-N-cyclohexyl-aminomethyl)-phenylamino)-1-methyl-methylene]-5-amido-2-indolinone (126) 3-Z-[1-(4-(N-(4-nitro-phenethyl)-N-isopropyl-aminomethyl)-phenylamino)-1-methyl-methylene]-5-amido-2-indolinone (127) 3-Z-[1-(4-(N-(2-(pyridin-2-yl)-ethyl)-N-methyl-amino-methyl)-phenylamino)-1-methyl-methylene]-5-amido-2-indolinone $C_{26}H_{27}N_5O_2$ mass spectrum: m/z=441 (M$^+$)

$R_f$ value: 0,51 (silica gel, methylene chloride/methanol=4:1)

(128) 3-Z-[1-(4-(N-(2-(pyridin-4-yl)-ethyl)-N-methyl-amino-methyl)-phenylamino)-1-methyl-methylene]-5-amido-2-indolinone (129) 3-Z-[1-(4-(N-(pyridin-2-yl-methyl)-N-methyl-amino-methyl)-phenylamino)-1methyl-methylene]-5-amido-2-indolinone (130) 3-Z-[1-(4-(N-(pyridin-3-yl-methyl)-N-methyl-amino-methyl)-phenylamino)-1-methyl-methylene]-5-amido-2-indolinone (131) 3-Z-[1-(4-(N-(pyridin-4-yl-methyl)-N-methyl-amino-methyl)-phenylamino)-1-methyl-methylene]-5-amido-2-indolinone (132) 3-Z-[1-(4-(dibenzylamino-methyl)-phenylamino)-1-methyl-methylene]-5-amido-2-indolinone $C_{32}H_{30}N_4O_2$ mass spectrum: m/z=503 (M+H$^+$)

$R_f$ value: 0,47 (silica gel, methylene chloride/methanol=9:1)

(133) 3-Z-[1-(4-(N-(4-nitro-benzyl)-N-propyl-aminomethyl)-phenylamino)-1-methyl-methylene]-5-amido-2-indolinone (134) 3-Z-[1-(4-(N-benzyl-N-(3-cyano-propyl)-aminomethyl)-phenylamino)-1-methyl-methylene]-5-amido-2-indolinone (135) 3-Z-[1-(4-(N-benzyl-N-allyl-aminomethyl)-phenylamino)-1-methyl-methylene]-5-amido-2-indolinone $C_{28}H_{26}N_4O_2$ mass spectrum: m/z=451 (M+H$^+$)

$R_f$ value: 0,53 (silica gel, methylene chloride/methanol=9:1)

(136) 3-Z-[1-(4-(imidazol-1-yl-methyl)-phenylamino)-1-methyl-methylene]-5-amido-2-indolinone $C_{21}H_{20}N_6O_2$ mass spectrum: m/z=389 (M+H$^+$)

$R_f$ value: 0,20 (silica gel, methylene chloride/methanol=4:1)

(137) 3-Z-[1-(4-(imidazol-2-yl-amino-methyl)-phenylamino)-1-methyl-methylene]-5-amido-2-indolinone (138) 3-Z-[1-(4-(N-benzyl-N-(2,2,2-trifluoroethyl)-aminomethyl)-phenylamino)-1-methyl-methylene]-5-amido-2-indolinone (139) 3-Z-[1-(4-(N-(benzo(1,3)dioxol-5-yl-methyl)-N-methyl-aminomethyl)-phenylamino)-1-methyl-methylene]-5-amido-2-indolinone $C_{27}H_{26}N_4O_4$ mass spectrum: m/z=470 (M+H$^+$)

$R_f$ value: 0,50 (silica gel, methylene chloride/methanol=9:1)

(140) 3-Z-[1-(4-(7-chloro-2,3,4,5-tetrahydro-benzo(d)azepin-3-yl-methyl)-phenylamino)-1-methyl-methylene]-5-amido-2-indolinone (141) 3-Z-[1-(4-(7,8-dichloro-2,3,4,5-tetrahydro-benzo(d)azepin-3-yl-methyl)-phenylamino)-1-methyl-methylene]-5-amido-2-indolinone (142) 3-Z-[1-(4-(7-bromo-2,3,4,5-tetrahydro-benzo(d)azepin-3-yl-methyl)-phenylamino)-1-methyl-methylene]-5-amido-2-indolinone (143) 3-Z-[1-(4-(7-fluoro-2,3,4,5-tetrahydro-benzo(d)azepin-3-yl-methyl)-phenylamino)-1-methyl-methylene]-5-amido-2-indolinone (144) 3-Z-[1-(4-(7-methoxy-2,3,4,5-tetrahydro-benzo(d)azepin-3-yl-methyl)-phenylamino)-1-methyl-methylene]-5-amido-2-indolinone (145) 3-Z-[1-(4-(7-methyl-2,3,4,5-tetrahydro-benzo(d)azepin-3-yl-methyl)-phenylamino)-1-methyl-methylene]-5-amido-2-indolinone (146) 3-Z-[1-(4-(7,8-dimethoxy-2,3,4,5-tetrahydro-benzo(d)azepin-3-yl-methyl)-phenylamino)-1-methyl-methylene]-5-amido-2-indolinone (147) 3-Z-[1-(4-(6,7-dichloro-1,2,3,4-tetrahydro-isoquinolin-2-yl-methyl)-phenylamino)-1-methyl-methylene]-5-amido-2-indolinone (148) 3-Z-[1-(4-(6,7-dimethyl-1,2,3,4-tetrahydro-isoquinolin-2-yl-methyl)-phenylamino)-1-methyl-methylene]-5-amido-2-indolinone (149) 3-Z-[1-(4-(6,7-difluoro-1,2,3,4-tetrahydro-isoquinolin-2-yl-methyl)-phenylamino)-1-methyl-methylene]-5-amido-2-indolinone $C_{27}H_{26}N_4O_2$ mass spectrum: m/z=439 (M+H$^+$)

$R_f$ value: 0,43 (silica gel, methylene chloride/methanol=9:1)

(150) 3-Z-[1-(4-(6-chloro-1,2,3,4-tetrahydro-isoquinolin-2-yl-methyl)-phenylamino)-1-methyl-methylene]-5-amido-2-indolinone (151) 3-Z-[1-(4-(7-chloro-1,2,3,4-tetrahydro-isoquinolin-2-yl-methyl)-phenylamino)-1-methyl-methylene]-5-amido-2-indolinone (152) 3-Z-[1-(4-(6-methoxy-1,2,3,4-tetrahydro-isoquinolin-2-yl-methyl)-phenylamino)-1-methyl-methylene]-5-amido-2-indolinone (153) 3-Z-[1-(4-(7-methoxy-1,2,3,4-tetrahydro-isoquinolin-2-yl-methyl)-phenylamino)-1-methyl-methylene]-5-amido-2-indolinone (154) 3-Z-[1-(4-(2,3,4,5-tetrahydro-azepino(4,5-b)pyrazin-3-yl-methyl)-phenylamino)-1-methyl-methylene]-5-amido-2-indolinone (155) 3-Z-[1-(4-(7-Amino-2,3,4,5-tetrahydro-azepino(4,5-b)pyrazin-3-yl-methyl)-phenylamino)-1-methyl-methylene]-5-amido-2-indolinone (156) 3-Z-[1-(4-(2-amino-5,6,7,8-tetrahydro-azepino(4,5-d)thiazol-6-yl-methyl)-phenylamino)-1-methyl-methylene]-5-amido-2-indolinone (157) 3-Z-[1-(4-(5,6,7,8-tetrahydro-azepino(4,5-d)thiazol-6-yl-methyl)-phenylamino)-1-methyl-methylene]-5-amido-2-indolinone (158) 3-Z-[1-(pyridin-3-yl-amino)-1-methyl-methylene]-5-amido-2-indolinone (159) 3-Z-[1-(thiazol-2-yl-amino)-1-methyl-methylene]-5-amido-2-indolinone (160) 3-Z-[1-(benzimidazol-2-yl-amino)-1-methyl-methylene]-5-amido-2-indolinone (161) 3-Z-[1-(5-methyl-isoxazol-3-yl-amino)-1-methyl-methylene]-5-amido-2-indolinone (162) 3-Z-[1-(imidazol-2-yl-amino)-1-methyl-methylene]-5-amido-2-indolinone (163) 3-Z-[1-(5-methyl-pyridin-2-yl-amino)-1-methyl-methylene]-5-amido-2-indolinone (164) 3-Z-[1-(5-bromo-pyridin-2-yl-amino)-1-methyl-methylene ]-5-amido-2-indolinone (165) 3-Z-[1-(2-chloro-pyridin-5-yl-amino)-1-methyl-methylene]-5-amido-2-indolinone (166) 3-Z-[1-(4-(N-butyl-N-methyl-aminomethyl)-phenylamino)-1-methyl-methylene]-5-amido-2-indolinone
$C_{23}H_{28}N_4O_2$
mass spectrum: m/z=392 (M$^+$)

(167) 3-Z-[1-(4-(N-isobutyl-aminomethyl)-phenylamino)-1-methyl-methylene]-5-amido-2-indolinone
$C_{22}H_{26}N_4O_2$
mass spectrum: m/z=378 (M$^+$)

(168) 3-Z-[1-(4-(N-cyclohexylmethyl-aminomethyl)-phenylamino)-1-methyl-methylene]-5-amido-2-indolinone
$C_{25}H_{30}N_4O_2$
mass spectrum: m/z=418
R$_f$ value: 0,26 (silica gel, methylene chloride/methanol= 4:1)

EXAMPLE 2

3-Z-[1-(4-Diethylcarbamoyl-phenylamino)1-methyl-methylene]-5-amido-2-indolinone 2 g of the resin prepared in Example IVb are reacted analogously to Example 1 with 2 g of ethyl 4-aminobenzoate in dimethylformamide at 110° C. The moist charged resin is suspended in 15 ml of dioxane and 15 ml of methanol and stirred with 12 ml of 1N sodium hydroxide solution for 40 hours. Then the mixture is neutralised with dilute hydrochloric acid and washed with methylene chloride, methanol and dimethylformamide. 300 mg of the resin are then suspended in 3 ml of dimethylformamide and left to stand with 0.2 ml of diethylamine, 0.5 g of TBTU (O-benzotriazol-1-yl-N,N,N',N'-tetramethyluronium-tetrafluoroborate), and 0.8 ml of N-ethyl-diisopropylamine for 40 hours at ambient temperature. Finally, the product is cleaved from the resin as described in Example 1.

Yield: 61 mg,

R$_f$ value: 0.30 (silica gel, methylene chloride/methanol= 9:1)

$C_{22}H_{24}N_4O_3$
mass spectrum: m/z=392 (M$^+$)

The following compounds are prepared analogously to Example 2:

(1) 3-Z-[1-(4-benzylcarbamoyl-phenylamino)-1-phenyl-methylene]-5-amido-2-indolinone
Prepared analogously to Example 2 with benzylamine
R$_f$ value: 0.30 (silica gel, methylene chloride/methanol= 9:1)
$C_{25}H_{22}N_4O_3$
mass spectrum: m/z=426 (M$^+$)

(2) 3-Z-[1-(4-(N-methoxycarbonylmethyl-carbamoyl)-phenylamino)-1-phenyl-methylene]-5-amido-2-indolinone
Prepared analogously to Example 2 with glycinethyl ester
R$_f$ value: 0.50 (silica gel, methylene chloride/methanol= 9:1)
$C_{21}H_{20}N_4O_5$
mass spectrum: m/z=408 (M$^+$)

(3) 3-Z-[1-(4-dimethylcarbamoyl-phenylamino)-1-phenyl-methylene]-5-amido-2-indolinone
Prepared analogously to Example 2 with dimethylamine
R$_f$ value: 0.40 (silica gel, methylene chloride/methanol= 9:1)
$C_{20}H_{20}N_4O_3$
mass spectrum: m/z=364 (M$^+$)

(4) 3-Z-[1-(4-(N-(2-piperidino-ethyl)-carbamoyl)-phenylamino)-1-methyl-methylene]-5-amido-2-indolinone-trifluoroacetate
Prepared analogously to Example 2 with 1-(2-amino-ethyl)-piperidine
R$_f$ value: 0.30 (silica gel, methylene chloride/methanol= 4:1)
$C_{25}H_{29}N_5O_3$
mass spectrum: m/z=448 (M+H$^+$)

(5) 3-Z-[1-(4-(N-methyl-piperazino-carbamoyl)-phenylamino)-1-phenyl-methylene]-5-amido-2-indolinone-trifluoroacetate
Prepared analogously to Example 2 with N-methyl-piperazine
R$_f$ value: 0.40 (silica gel, methylene chloride/methanol= 4:1)
$C_{23}H_{25}N_5O_3$
mass spectrum: m/z=419 (M$^+$)

(6) 3-Z-[1-(4-(N-(2-Diethylamino-ethyl)-N-methyl-carbamoyl)-phenylamino)-1-phenyl-methylene]-5-amido-2-indolinone-trifluoroacetate
Prepared analogously to Example 2 with N,N-diethyl-N'-methyl-ethylenediamine
R$_f$ value: 0.20 (silica gel, methylene chloride/methanol= 4:1)
$C_{25}H_{31}N_5O_3$
mass spectrum: m/z=449 (M$^+$)

(7) 3-Z-[1-(4-Butylcarbamoyl-phenylamino)-1-phenyl-methylene]-5-amido-2-indolinone
Prepared analogously to Example 2 with butylamine
R$_f$ value: 0.80 (silica gel, methylene chloride/methanol= 4:1)
$C_{22}H_{24}N_4O_3$
mass spectrum: m/z=392 (M$^+$)

EXAMPLE 3

3-Z-[1-(4-(N-methyl-N-benzoyl-amino)-phenylamino)-1-methyl-methylene]-5-amido-2-indolinone 4.5 g of a resin prepared according to Example IVb are reacted analogously to Example 1 with 3.4 g of 4-(9H-fluoren-9-yl-methoxycarbonyl)-methylamino)-aniline in dimethylformamide. Then the 9H-fluoren-9-yl-methoxycarbonyl group is cleaved with 40 ml of 30% piperidine in dimethylformamide and the resin is washed several times. Then 400 mg of the resin are suspended in 4 ml of dimethylformamide and 0.3 ml of triethylamine and reacted with 0.3 ml of benzoylchloride for one hour at ambient temperature. Finally, the product is cleaved from the resin with trifluoroacetic acid as described in Example 1.

Yield: 25 mg, p $R_f$ value: 0.51 (silica gel, methylene chloride/methanol=9:1)

$C_{30}H_{24}N_4O_3$ mass spectrum: m/z=426 ($M^+$)

The following compounds are prepared analogously to Example 3:

(1) 3-Z-[1-(4-(N-methyl-N-propionyl-amino)-phenylamino)-1-methyl-methylene]-5-amido-2-indolinone Prepared analogously to Example 3 with propionic acid chloride $R_f$ value: 0.52 (silica gel, methylene chloride/methanol=9:1)

$C_{21}H_{22}N_4O_3$ mass spectrum: m/z=378 ($M^+$)

(2) 3-Z-[1-(4-(N-methyl-N-butyryl-amino)-phenylamino)-1-methyl-methylene]-5-amido-2-indolinone Prepared analogously to Example 3 with butyric acid chloride $R_f$ value: 0.28 (silica gel, methylene chloride/methanol=9:1)

$C_{22}H_{24}N_4O_3$ mass spectrum: m/z=392 ($M^+$)

(3) 3-Z-[1-(4-(N-methyl-N-ethanesulphonyl-amino)-phenylamino)-1-methyl-methylene]-5-amido-2-indolinone Prepared analogously to Example 3 with ethanesulphonic acid chloride $R_f$ value: 0.30 (silica gel, methylene chloride/methanol=9:1)

$C_{20}H_{22}N_4O_4S$ mass spectrum: m/z=413 (M–$H^+$)

(4) 3-Z-[1-(4-(N-methyl-N-propanesulphonyl-amino)-phenylamino)-1-methyl-methylene]-5-amido-2-indolinone Prepared analogously to Example 3 with propanesulphonic acid chloride $R_f$ value: 0.31 (silica gel, methylene chloride/methanol=9:1)

$C_{21}H_{24}N_4O_4S$ mass spectrum: m/z=451 (M+$Na^+$)

(5) 3-Z-[1-(4-(N-methyl-N-phenylsulphonylamino)-phenylamino-1-methyl-methylene]-5-amido-2-indolinone Prepared analogously to Example 3 with phenylsulphonic acid chloride $R_f$ value: 0.46 (silica gel, methylene chloride/methanol=9:1)

$C_{24}H_{22}N_4O_4S$ mass spectrum: m/z=462 ($M^+$)

(6) 3-Z-[1-(4-(N-methyl-N-acetyl-amino)-phenylamino)-1-methyl-methylene]-5-amido-2-indolinone Prepared analogously to Example 3 with acetylchloride $R_f$ value: 0.20 (silica gel, methylene chloride/methanol=9:1)

$C_{20}H_{20}N_4O_3$ mass spectrum: m/z=364 ($M^+$)

(7) 3-Z-[1-(4-(N-methyl-N-phenylmethylsulphonyl-amino)-phenylamino)-1-methyl-methylene]-5-amido-2-indolinone Prepared analogously to Example 3 with phenylmethanesulphonic acid chloride $R_f$ value: 0.43 (silica gel, methylene chloride/methanol=9:1)

$C_{25}H_{24}N_4O_4S$ mass spectrum: m/z=475 (M–$H^+$)

EXAMPLE 4

Methyl 3-Z-[1-(4-(N-benzyl-N-methyl-aminomethyl)-phenylamino)-1-methyl-methylene]-2-indolinone-5-carboxylate 8.0 g (28 mmol) of methyl 1-acetyl-3-(1-ethoxy-1-methyl-methylene)-2-indolinone-5-carboxylate are dissolved in 60 ml of dimethylformamide and stirred with 6.3 g (28 mmol) of 4-(N-benzyl-N-methyl-aminomethyl)-aniline for 6 hours at 80° C. Then 30 ml of conc. ammonia are added and the mixture is left to stand for 2 hours at 45° C.

The solution is evaporated down and the residue is washed with ethanol and ether.

Then it is chromatographed over a small silica gel column with ethyl acetate/ethanol (9:1).

Yield: 8.6 g (70% of theory), melting point: 150–152° C.

$C_{27}H_{27}N_3O_3$ mass spectrum: m/z=442 ($M^+$)

The following compounds are prepared analogously to Example 4:

(1) methyl 3-Z-[1-(4-(piperidino-methyl)-phenylamino)-1-methyl-methylene]-2-indolinone-5-carboxylate $C_{24}H_{27}N_3O_3$ mass spectrum: m/z=406 (M+$H^+$)

(2) methyl 3-Z-[1-(4-bromo-phenylamino)-1-methyl-methylene]-2-indolinone-5-carboxylate $C_{18}H_{15}BrN_2O_3$ mass spectrum: m/z=386/388 ($M^+$)

(3) methyl 3-Z-[1-(4-chloro-phenylamino)-1-methyl-methylene]-2-indolinone-5-carboxylate $C_{18}H_{15}ClN_2O_3$ mass spectrum: m/z=342/344 ($M^+$)

(4) methyl 3-Z-[1-(4-(N-methyl-N-methylsulphonyl-amino)-phenylamino)-1-ethyl-methylene]-2-indolinone-5-carboxylate $C_{20}H_{21}N_3O_5S$ mass spectrum: m/z=415 ($M^+$)

(5) methyl 3-Z-[1-(4-(2,3,4,5-tetrahydro-benzo(d)azepin-3-yl-methyl)-phenylamino)-1-methyl-methylene]-2-indolinone-5-carboxylate
$C_{29}H_{29}N_3O_2$
mass spectrum: m/z=467 (M$^+$)

EXAMPLE 5

3-Z-[1-(4-(N-benzyl-N-methyl-aminomethyl)-phenylamino)-1-methyl-methylene]-2-indolinone-5-carboxylic acid 2.3 g (5 mmol) of methyl 3-Z-[1-(4-(N-benzyl-N-methyl-aminomethyl)-phenylamino)1-methyl-methylene]-2-indolinone-5-carboxylate are dissolved in 50 ml of methanol and 50 ml of dioxane and stirred with 25 ml of 1N sodium hydroxide solution for I hour at 70° C. Then the mixture is neutralised with 25 ml of 1N hydrochloric acid and evaporated to dryness. The residue is washed several times with water and dried.

Yield: 1.9 g (85% of theory),
$C_{26}H_{25}N_3O_3$
mass spectrum: m/z=428 (M+H$^+$)

The following compounds are prepared analogously to Example 5:

(1) 3-Z-[1-(4-(Piperidino-methyl)-phenylamino)-1-methyl-methylene]-2-indolinone-5-carboxylic acid
$C_{23}H_{25}N_3O_3$
mass spectrum: m/z=392 (M+H$^+$)

(2) 3-Z-[1-(4-bromo-phenylamino)-1-methyl-methylene]-2-indolinone-5-carboxylic acid (3) 3-Z-[1-(4-chloro-phenylamino)-1-methyl-methylene]-2-indolinone-5-carboxylic acid
$C_{17}H_{13}ClN_2O_3$
mass spectrum: m/z=327/329 (M–H$^+$)

(4) 3-Z-[1-(4-(N-methyl-N-methylsulphonyl-amino)-phenylamino)-1-methyl-methylene]-2-indolinone-5-carboxylic acid
$C_{19}H_{19}N_3O_5S$
mass spectrum: m/z=401 (M$^+$)

(5) 3-Z-[1-(4-(2,3,4,5-tetrahydro-benzo(d)azepin-3-yl-methyl)-phenylamino)-1-methyl-methylene]-2-indolinone-5-carboxylic acid
$C_{28}H_{27}N_3O_3$
mass spectrum: m/z=453 (M$^+$)

EXAMPLE 6

3-Z-[1-(4-(N-benzyl-N-methyl-aminomethyl)-phenylamino)-1-methyl-methylene]-2-indolinone-5-diethylcarbamoyl-2-indolinone 0.3 g of 3-Z-[1-(4-(N-benzyl-N-methyl-aminomethyl)-phenylamino)-1-methyl-methylene]-2-indolinone-2-indolinone-5-carboxylic acid are dissolved with 1.2 g of N-ethyl-diisopropylethylamine in 8 ml of dimethylformamide. Then 0. 1 g of diethylamine and 0.4 g of TBTU (O-benzotriazol-1-yl-N,N,N',N'-tetramethyluronium-tetrafluoroborate) are added and the mixture is stirred for 20 hours at ambient temperature. It is then evaporated down and the residue is suspended in water and extracted with methylene chloride. The organic phase is evaporated down and chromatographed over a silica gel column with methylene chloride/ethanol (19:1).

Yield: 0.2 g (68% of theory),
R$_f$ value: 0.36 (silica gel, methylene chloride/ethanol= 19:1)
$C_{30}H_{34}N_4O_2$
mass spectrum: m/z=482 (M$^+$)

The following compounds are prepared analogously to Example 6:

(1) 3-Z-[1-(4-(Piperidino-methyl)-phenylamino)-1-methyl-methylene]-2-indolinone-5-diethylcarbamoyl-2-indolinone
Prepared from the compound produced in Example 5(1) and diethylamine
$C_{27}H_{34}N_4O_2$
mass spectrum: m/z=446 (M$^+$)

(2) 3-Z-[1-(4-(N-methyl-N-methylsulphonyl-amino)-phenylamino)-1-methyl-methylene]-2-indolinone-5-diethylcarbamoyl-2-indolinone
Prepared from the compound produced in Example 5(4) and diethylamine
$C_{23}H_{28}N_4O_4S$
mass spectrum: m/z=457 (M+H$^+$)

(3) 3-Z-[1-(4-(2,3,4,5-tetrahydro-benzo(d)azepin-3-yl-methyl)-phenylamino)-1-methyl-methylene]-5-diethylcarbamoyl-2-indolinone (4) 3-Z-[1-(4-(2,3,4,5-tetrahydro-benzo(d)azepin-3-yl-methyl)-phenylamino)-1-methyl-methylene]-5-dimethylcarbamoyl-2-indolinone (5) 3-Z-[1-(4-(N-Phenylmethyl-N-methylamino-methyl)-phenylamino)-1-methyl-methylene]-5-methylcarbamoyl-2-indolinone (6) 3-Z-[1-(4-(N-Phenylmethyl-N-methylamino-methyl)-phenylamino)-1-methyl-methylene]-5-dimethylcarbamoyl-2-indolinone (7) 3-Z-[1-(4-(N-Phenylmethyl-N-methylamino-methyl)-phenylamino)-1-methyl-methylene]-5-diethylcarbamoyl-2-indolinone (8) 3-Z-[1-(4-(N-Phenylmethyl-N-methylamino-methyl)-phenylamino)-1-methyl-methylene]-5-propylcarbamoyl-2-indolinone (9) 3-Z-[1-(4-(N-Phenylmethyl-N-methylamino-methyl)-phenylamino)-1-methyl-methylene]-5-dipropylcarbamoyl-2-indolinone

(10) 3-Z-[1-(4-(dimethylamino-methyl)-phenylamino)-1-methyl-methylene]-5-methylcarbamoyl-2-indolinone

(11) 3-Z-[1-(4-(dimethylamino-methyl)-phenylamino)-1-methyl-methylene]-5-dimethylcarbamoyl-2-indolinone

(12) 3-Z-[1-(4-(dimethylamino-methyl)-phenylamino)-1-methyl-methylene]-5-diethylcarbamoyl-2-indolinone

(13) 3-Z-[1-(4-(dimethylamino-methyl)-phenylamino)-1-methyl-methylene]-5-propylcarbamoyl-2-indolinone

(14) 3-Z-[1-(4-(dimethylamino-methyl)-phenylamino)-1-methyl-methylene]-5-dipropylcarbamoyl-2-indolinone

(15) 3-Z-[1-(3-(dimethylamino-methyl)-phenylamino)-1-methyl-methylene]-5-methylcarbamoyl-2-indolinone

(16) 3-Z-[1-(3-(dimethylamino-methyl)-phenylamino)-1-methyl-methylene]-5-dimethylcarbamoyl-2-indolinone

(17) 3-Z-[1-(3-(dimethylamino-methyl)-phenylamino)-1-methyl-methylene]-5-diethylcarbamoyl-2-indolinone

(18) 3-Z-[1-(3-(dimethylamino-methyl)-phenylamino)-1-methyl-methylene]-5-propylcarbamoyl-2-indolinone

(19) 3-Z-[1-(3-(dimethylamino-methyl)-phenylamino)-1-methyl-methylene]-5-dipropylcarbamoyl-2-indolinone

(20) 3-Z-[1-(4-chloro-phenylamino)-1-methyl-methylene]-5-methylcarbamoyl-2-indolinone

(21) 3-Z-[1-(4-chloro-phenylamino)-1-methyl-methylene]-5-dimethylcarbamoyl-2-indolinone
(22) 3-Z-[1-(4-chloro-phenylamino)-1-methyl-methylene]-5-diethylcarbamoyl-2-indolinone
(23) 3-Z-[1-(4-chloro-phenylamino)-1-methyl-methylene]-5-propylcarbamoyl-2-indolinone
(24) 3-Z-[1-(4-chloro-phenylamino)-1-methyl-methylene]-5-dipropylcarbamoyl-2-indolinone
(25) 3-Z-(1-phenylamino-1-methyl-methylene)-5-methylcarbamoyl-2-indolinone
(26) 3-Z-(1-phenylamino-1-methyl-methylene)-5-dimethylcarbamoyl-2-indolinone
(27) 3-Z-(1-Phenylamino-1-methyl-methylene)-5-diethylcarbamoyl-2-indolinone

EXAMPLE 7

3-Z-[1-(4-methyl-3-amino-phenylamino)-1-methyl-methylene]-5-amido-2-indolinone 130 mg of 3-Z-[1-(4-methyl-3-nitro-phenylamino)-1-methyl-methylene]-5-amido-2-indolinone are dissolved in 9 ml of methanol and hydrogenated with 50 mg of Raney nickel at ambient temperature under 3 bar of hydrogen pressure. The catalyst is filtered off and the solution is evaporated down.

Yield: 97 mg (70% of theory), $R_f$ value: 0.60 (silica gel, methylene chloride/Ethanol=4:1)

$C_{18}H_{18}N_4O_2$ mass spectrum: m/z=322 ($M^+$)

The following compound is prepared analogously to Example 7:

(1) 3-Z-[1-(4-(piperidino-methyl)-3-amino-phenylamino)-1-methyl-methylene]-5-amido-2-indolinone
Prepared aus 3-Z-[1-(4-(piperidino-methyl)-3-nitro-phenylamino)-1-methyl-methylene]-5-amido-2-indolinone
$R_f$ value: 0,15 (silica gel, methylene chloride/ethanol=9:1)
$C_{23}H_{27}N_5O_2$
mass spectrum: m/z=406 ($M+H^+$)

EXAMPLE 8

Dry Ampoule Containing 75 mg of Active Substance Per 10 ml

Composition:

| | |
|---|---|
| Active substance | 75.0 mg |
| Mannitol | 50.0 mg |
| water for injections | ad 10.0 ml |

Preparation:

Active substance and mannitol are dissolved in water. After packaging the solution is freeze-dried. To produce the solution ready for use, the product is dissolved in water for injections.

EXAMPLE 9

Dry Ampoule Containing 35 mg of Active Substance Per 2 ml

Composition:

| | |
|---|---|
| Active substance | 35.0 mg |
| Mannitol | 100.0 mg |
| water for injections | ad 2.0 ml |

Preparation:

Active substance and mannitol are dissolved in water. After packaging, the solution is freeze-dried.

To produce the solution ready for use, the product is dissolved in water for injections.

EXAMPLE 10

Tablet Containing 50 mg of Active Substance

Composition:

| | |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

EXAMPLE 11

Tablet Containing 350 mg of Active Substance

Composition:

| | |
|---|---|
| (1) Active substance | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

EXAMPLE 12

Capsules Containing 50 mg of Active Substance

Composition:

| | |
|---|---|
| (1) Active substance | 50.0 mg |
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing.

This powder mixture is packed into size 3 hard gelatin capsules in a capsule filling machine.

EXAMPLE 13

Capsules Containing 350 mg of Active Substance

Composition:

| | |
|---|---|
| (1) Active substance | 350.0 mg |
| (2) Dried maize starch | 46.0 mg |
| (3) Powdered lactose | 30.0 mg |
| (4) Magnesium stearate | 4.0 mg |
| | 430.0 mg |

Preparation:

(1) is triturated with (3). This trituration is added to the mixture of (2) and (4) with vigorous mixing.

This powder mixture is packed into size 0 hard gelatin capsules in a capsule filling machine.

EXAMPLE 14

Suppositories Containing 100 mg of Active Substance 1 suppository contains:

| | |
|---|---|
| Active substance | 100.0 mg |
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

Preparation:

The polyethyleneglycol is melted with the polyethylenesorbitan monostearate. The milled active substance is homogeneously dispersed in the melt at 40° C. The melt is cooled to 38° C. and poured into lightly pre-cooled suppository moulds.

What is claimed is:

1. A compound of the formula

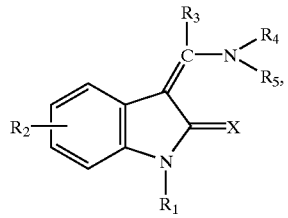

(I)

wherein:

X denotes an oxygen or sulphur atom, $R_1$ denotes a hydrogen atom, a $C_{1-4}$-alkoxy-carbonyl or $C_{2-4}$-alkanoyl group, $R_2$ denotes a carboxy or $C_{1-4}$-alkoxy-carbonyl group or an aminocarbonyl group optionally substituted by one or two $C_{1-3}$-alkyl groups, whilst the substituents may be identical or different, $R_3$ denotes a hydrogen atom or a $C_{1-6}$-alkyl group which may be substituted at the 2 position, in relation to the carbon atom of the $R_3$-C($R_4NR_5$)= group by a fluorine, chlorine or bromine atom, by a hydroxy, $C_{1-3}$-alkoxy, $C_{1-3}$-alkylsulphenyl, $C_{1-3}$-alkylsulphinyl, $C_{1-3}$-alkylsulphonyl, phenylsulphenyl, phenylsulphinyl, phenylsulphonyl, amino, $C_{1-3}$-alkylamino, di-($C_{1-3}$-alkyl)-amino, $C_{2-5}$-alkanoylamino or N-($C_{1-3}$-alkylamino)-$C_{2-5}$-alkanoylamino group, $R_4$ denotes a phenyl or naphthyl group which is substituted by a $C_{2-3}$-alkoxy group which is substituted in the 2 or 3 position by a 5- membered cycloalkyleneimino group, by a carbonyl group which is substituted by a 5-membered cycloalkyleneimino group, by a $C_{1-3}$-alkyl group which is substituted by a 5-membered cycloalkenyleneimino group or by a 4- to 5-membered cycloalkyleneimino group, wherein the abovementioned 5-membered cycloalkyleneimino groups may be substituted by one or two $C_{1-3}$-alkyl groups, by a $C_{5-7}$-cycloalkyl or phenyl group, by a $C_{1-3}$-alkyl, $C_{5-7}$-cycloalkyl, phenyl, carboxy or $C_{1-4}$-alkoxy-carbonyl group and by a hydroxy group and in the abovementioned cycloalkyleneimino groups a methylene group adjacent to the nitrogen atom may be replaced by a carbonyl group, or by a $C_{1-3}$-alkyl group which is substituted by a 5-membered cycloalkyleneimino group, whilst a phenyl group optionally mono- or disubstituted by fluorine, chlorine or bromine atoms or by methyl or methoxy groups, wherein the substituents may be identical or different, may be fused to the abovementioned 5-membered cycloalkyleneimino groups via two adjacent carbon atoms, whilst additionally the abovementioned monosubstituted phenyl groups may be substituted by a fluorine, chlorine or bromine atom or by a methyl, methoxy or nitro group, a 5-membered heteroaromatic group which contains an imino group, and $R_5$ denotes a hydrogen atom or a $C_{1-3}$-alkyl group whilst any carboxy, amino or imino groups present may be substituted by groups which can be cleaved in vivo, or a pharmaceutically acceptable salt thereof.

2. A compound of the formula I according to claim 1, wherein:

X denotes an oxygen atom, $R_1$ denotes a hydrogen atom, $R_2$ denotes an aminocarbonyl group, $R_3$ denotes a hydrogen atom or a $C_{1-4}$-alkyl group which may be substituted, at the 2 position in relation to the carbon atom of the $R_3$-C($R_4NR_5$)= group, by a chlorine or bromine atom or by a phenylsulphonyl group, $R_4$ denotes a phenyl group which is substituted
by a $C_{2-3}$-alkoxy group which is substituted in the 2 or 3 position by 5- membered cycloalkyleneimino group,
by a carbonyl group which is substituted by a 5-membered cycloalkyleneimino group,
by a $C_{1-3}$-alkyl group which is substituted by a 5-membered cycloalkenyleneimino group or by a 4- to 5-membered cycloalkyleneimino group, wherein the abovementioned 5-membered cycloalkyleneimino groups may be substituted by one or two $C_{1-3}$-alkyl groups, by a cyclohexyl or phenyl group, by a $C_{1-3}$-alkyl, cyclohexyl, phenyl, carboxy or $C_{1-4}$-alkoxy-carbonyl group and by a hydroxy group and in the abovementioned cycloalkyleneimino groups a methylene group adjacent to the nitrogen atom may be replaced by a carbonyl group,
by a $C_{1-3}$-alkyl group which is substituted by a 5-membered cycloalkyleneimino group, whilst a phenyl group optionally mono- or disubstituted by fluorine, chlorine or bromine atoms or by methyl or methoxy groups, wherein the substituents may be identical or different, may be fused to the abovementioned 5-membered cycloalkyleneimino groups via two adjacent carbon atoms, whilst additionally the abovementioned monosubstituted phenyl groups may be substituted by a fluorine, chlorine or bromine atom or by a methyl, methoxy or nitro group, $R_5$ denotes a hydrogen atom or a $C_{1-3}$-alkyl group, or a pharmaceutically acceptable salt thereof.

3. A compound of the formula I according to claim 2, wherein:

$R_2$ is in the 5 position, or a pharmaceutically acceptable salt thereof.

4. A compound of the formula I according to claim 1, wherein:

X denotes an oxygen atom, $R_1$ denotes a hydrogen atom, $R_2$ in the 5 position denotes an aminocarbonyl group, $R_3$ denotes a hydrogen atom or a $C_{1-4}$-alkyl group which may be terminally substituted by a chlorine or bromine atom or by a phenylsulphonyl group, $R_4$ denotes a phenyl group which may be substituted
by a methyl or ethyl group, which in each case is substituted by a 5-membered cycloalkenyleneimino group or by a 5-membered cycloalkyleneimino group, whilst the abovementioned 5-membered cycloalkyleneimino groups may be substituted by one or two methyl groups, by a cyclohexyl or phenyl group, by a methyl, cyclohexyl or phenyl group and by a hydroxy group, or
by a methyl or ethyl group which may be substituted by a phenyl group which is substituted by a 5-membered cycloalkyleneimino group, whilst additionally a phenyl ring is fused to the abovementioned cycloalkyleneimino groups via 2 adjacent carbon atoms, whilst additionally the abovementioned monosubstituted phenyl groups may be substituted by a fluorine, chlorine or bromine atom or by a methyl, methoxy or nitro group, and $R_5$ denotes a hydrogen atom or a $C_{1-4}$-alkyl group, or a pharmaceutically acceptable salt thereof.

5. A compound of the formula I according to claim 1, wherein:

X denotes an oxygen atom, $R_1$ denotes a hydrogen atom, $R_2$ in the 5 position denotes an aminocarbonyl group, $R_3$ denotes a hydrogen atom or a $C_{1-4}$-alkyl group, $R_4$ denotes a phenyl group which may be substituted
by a methyl or ethyl group, which is substituted in each case by a 5-membered cycloalkenyleneimino group or by a 5-membered cycloalkyleneimino group, whilst the abovementioned 5-membered cycloalkyleneimino groups may be substituted by one or two methyl groups, by a cyclohexyl or phenyl group, by a methyl, cyclohexyl or phenyl group and by a hydroxy group, or
by a methyl or ethyl group which may be substituted by a phenyl group which is substituted in the 4 position by a 5-membered cycloalkyleneimino group, whilst additionally a phenyl ring is fused to the abovementioned cycloalkyleneimino groups via 2 adjacent carbon atoms, whilst additionally the abovementioned monosubstituted phenyl groups may be substituted by a fluorine, chlorine or bromine atom or by a methyl, methoxy or nitro group, and $R_5$ denotes a hydrogen atom or a $C_{1-4}$-alkyl group, or a pharmaceutically acceptable salt thereof.

6. A compound selected from the group consisting of:

(a) 3-Z-[1-(4-pyrrolidinomethyl-phenylamino)-1-methyl-methylene]-5-amido-2-indolinone, (b) 3-Z-[1-[4-(2-ethoxycarbonyl-pyrrolidinomethyl)-phenylamino]-1-methyl-methylene]-5-amido-2-indolinone, (c) 3-Z-[1-[4-(2,5-Dihydropyrrol-1-yl-methyl)-phenylamino]-1-methyl-methylene]-5-amido-2-indolinone, (d) 3-Z-[1-(4-Azetidionomethyl-phenylamino)-1-methyl-methylene]-5-amido-2-indolinone and (e) 3-Z-[1-(4-(1,3-Dihydro-isoindol-2-yl-methyl)-phenylamino)-1-methyl-methylene]-5-amido-2-indolinone, or a pharmaceutically acceptable salt thereof.

7. 3-Z-[1-(4-Pyrrolidinomethyl-phenylamino)-1-methyl-methylene]-5-amido-2-indolinone or a pharmaceutically acceptable salt thereof.

8. A pharmaceutical composition comprising a compound in accordance with claim 1.

9. A method for treating excessive or anomalous cell proliferation which method comprises administering to a host in need of such treatment a cell proliferation-inhibiting amount of a compound in accordance with claim 1, 2, 3, 4, 5, 6 or 7.

10. A method for treating lymphoma or solid tumors which method comprises administering to a host in need of such treatment a therapeutic amount of a compound in accordance with claim 1, 2, 3, 4, 5, 6 or 7.

* * * * *